United States Patent [19]
Verwer et al.

[11] Patent Number: 5,605,805
[45] Date of Patent: Feb. 25, 1997

[54] AUTOMATIC LINEAGE ASSIGNMENT OF ACUTE LEUKEMIAS BY FLOW CYTOMETRY

[75] Inventors: Ben J. H. Verwer, San Jose; Leon W. M. M. Terstappen, Palo Alto, both of Calif.

[73] Assignee: Becton, Dickinson and Company, Franklin Lakes, N.J.

[21] Appl. No.: 326,153

[22] Filed: Oct. 19, 1994

Related U.S. Application Data

[63] Continuation-in-part of Ser. No. 15,709, Feb. 9, 1993, abandoned.

[51] Int. Cl.$^6$ ............... G01N 33/536; G01N 33/574; G01N 33/49; G01N 21/64
[52] U.S. Cl. ............ 435/7.24; 435/968; 435/973; 436/548; 436/536; 436/172; 436/800; 436/813; 356/39; 356/337; 364/555; 382/134
[58] Field of Search ................... 435/7.24, 968, 435/973; 436/548, 536, 172, 800, 813; 356/39, 337; 364/413.08, 555; 382/6, 36

[56] References Cited

U.S. PATENT DOCUMENTS

| | | | |
|---|---|---|---|
| 4,661,913 | 4/1987 | Wu et al. | 364/500 |
| 4,845,653 | 7/1989 | Conrad et al. | 364/521 |
| 5,234,816 | 8/1993 | Terstappen . | |

OTHER PUBLICATIONS

L. Terstappen, et al. "Five Dimensional Flow Cytometry as a New Approach for Blood and Bone Marrow Differentials" *Cytometry* 9, 548–556 (1988).
J. Robinson, et al. "An Innovation in Flow Cytometry Data Collection and Analyisi Producing a Corelated Multiple Sample Analysis in a Single File" *Cytometry* 12, 82–90 (1991).
y. Kosugi, et al. "An Interactive Multivariate Analysis of FCM Data" *Cytometry* 9, 405–408 (1988).
L. Terstappen, et al. "Flow Cytometric Characterization of Acute Myeloid Leukemia. Part II. Phenotypic Heterogeneity at Diagnosis" *Leukemia* 5, 757–767 (1991).
E. Archimbaud, et al. "Expression of Surface Adhesion Molecules CD54 (ICAM–1) and CD58 (LFA–3) in Adult Acute Leukemia: Relationship with Initial Characteristics and Prognosis" *Leukemia* 6:265–271 Apr. 1992.
M. J. Borowitz et al. "Clinicopathologic and Cytogenic Features of CD34 (My10)–Positive Acute Nonlymphocytic Leukemia" *Am. J. Clin. Pathol.* 91:265–270 (1989).
W. Crist, et al. "Prognostic Importance of the Pre–B–Cell Immunophenotype and Other Presenting Features in B–Lineage Childhood Acute Lymphoblastic Leukemia: A Pediatric Oncology Group Study" *Blood* 74:1252–1259 (1989).
L. Campos, et al. "Surface marker expression in adult acute myeloid leukaemia: correlations with initial characteristics, morphology and response to therapy" *Brit. J. Haematology* 72:161–166 (1989).

H. G. Drexler "Classification of Acute Myeloid Leukemias –A Comparison of FAB and Immunophenotyping" *Leukemia* 1:697–705 (1987).
K. A. Foon, et al. "Immunologic Classification of Leukemia and Lymphoma" *Blood* 68:1–31 (1986).
D. S. Frankel, et al. "Use of a Neural Net Computer System for Analysis of Flow Cytometric Data of Phytoplankton Populations" *Cytometry* 10:540–550 (1989).
K. C. Gowda, et al. "Agglomerative Clustering Using the Concept of Mutual Nearest Neighbourhood" *Pattern Recognition* 10:105–112 (1978).
M. F. Greaves, et al. "Lineage Promiscuity in Hemopoietic Differentiation and Leukemia" *Blood* 67:1–11 (1986).
J. D. Griffin, et al. "Use of Surface Marker Analysis to Predict Outcome of Adult Acute Myeloblastic Leukemia" *Blood* 68:1232–1241 (1986).
D. Hoelzer, et al. "Prognostic Factors in a Multicenter Study for Treatment of Acute Lymphoblastic Leukemia in Adults" *Blood* 71:123–131 (1988).
C. A. Hurwitz, et al. "Asynchronous Antigen Expression in B Lineage Acute Lymphoblastic Leukemia" *Blood* 72:299–307 (1988).
G. Janossy, et al. "The pathophysiological basis of immunodiagnosis in acute lymphoblastic leukemia" *Cancer Rev.* 8:91–122 (1988).
M. Keinänen, et al. "Clonal Chromosomal Abnormalities Showing Multiple–Cell–Lineage Involvement in Acute Myeloid Leukemia" *N. Engl. J. Med.* 318:1153–1158 (1988).
B. S. Kim, et al. "A Fast k Nearest Neighbor Finding Algorithm Based on the Ordered Partition" *IEEE Transactions on Pattern Analysis and Machine Intelligence* vol. PAMI–8, pp. 761–766, 1986.
D. Frankel, et al. "Use of a Neural Net Computer System for Analysis of Flow Cytometric Data of Phytoplankton Populations" *Cytometry Suppl.* 2:29, Abst. #172 (1988).

(List continued on next page.)

*Primary Examiner*—James C. Housel
*Assistant Examiner*—Nancy J. Parsons
*Attorney, Agent, or Firm*—Donna R. Fugit

[57] ABSTRACT

A method for automatic lineage assignment of acute leukemias. Eight four-parameter list mode data files are acquired with a flow cytometer in the following sequence: 1. unstained; 2. isotype controls; 3. CD10 FITC, CD19 PE; 4. CD20 FITC, CD5 PE; 5. CD3 FITC, CD22 PE; 6. CD7 FITC, CD33 PE; 7. HLADR FITC, CD13 PE and 8. CD34 FITC, CD38 PE. First, data files 3–8 are clustered employing an algorithm based on nearest neighbors. The clusters are then associated across the data files to form cell populations, using the assumption of light scatter invariance across tubes for each population. The mean positions of each cell population are compared to a decision tree which identifies normal cell populations. To identify leukemic cell populations, the algorithm eliminates normal cell populations from the data space and the remaining populations are classified as B-lineage ALL, T-lineage ALL, AML, AUL, B-CLL or unknown.

3 Claims, 29 Drawing Sheets

(29 of 29 Drawing(s) in Color)

OTHER PUBLICATIONS

H. Merle–beral, et al. "Diagnostic and prognostic significance of myelomonocytic cell surface antigens in acute myeloid leukaemia" *Brit. J. Haematology* 73:323–330 (1989).

P. B. Neame, et al. "Simultaneous or Sequential Expression of Lymphoid and Myeloid Phenotypes in Acute Leukemia" *Blood* 65:142–148 (1985).

K. D. Sabbath, et al. "Heterogeneity of Clonogenic Cells in Acute Myeloblastic Leukemia" *J. Clin. Invest.* 75:746–753 (1985).

G. C. Salzman, et al. "3–D Autostereoscopic Viewing of Multidimensional Data for Guided Cluster Analysis" *Cytometry Suppl.* 5:64. Abst. #305 (1991).

J. F. San Miguel, et al., "Prognostic Value of Immunological Markers in Acute Myeloblastic Leukemia" *Leukemia* 3:108–111 (1989).

L. W. M. M. Testappen, et al. "Flow Cytometric Characterization of Acute Myeloid Leukemia. Part 1. Significance of Light Scattering Properties" *Leukemia* 5:315–321 (1991).

L. W. M. M. Terstappen, et al. "Flow Cytometric Characterization of Acute Myeloid Leukemia: IV. Comparison to the Differentiation Pathway of Normal Hematopoietic Progenitor Cells" *Leukemia* 6:993–1000, Oct. 1992.

L. W. M. M. Terstappen, et al. "Flow Cytometric Assessment of Human T–Cell Differentiation in Thymus and Bone Marrow" *Blood* 79:666–677, Feb. 1, 1992.

L. W. M. M. Terstappen, et al. "Increased Light Scattering Resolutioin Facilitates Multidimensional Flow Cytometric Analysis" *Cytometry* 11:506–512 (1990).

L. W. M M. Terstappen, et al. "Quantitative Comparison of Myeloid–Antigens on Five Lineages of Mature Peripheral Blood Cells" *J. Leukocyte Biol.* 48:138–148 (1990).

J. Tucker, et al. "Immunophenotype of Blast Cells in Acute Myeloid Leukemia May Be a Useful Predictive Factor for Outcome" *Hematol. Oncol.* 8:47–58 (1990).

D. L. White, et al. "The Expression of Mature Myeloid Cell Differentiation Markers in Acute Leukemia" *Pathology* 19:137–142 (1987).

| | | |
|---|---|---|
| S1 ■ | ERTHROID | (A1234, B123) |
| S2 ■ | LYMPHOCYTES | (B1-C2) |
| S3 ■ | STEMCELLS | (C1-D2) |
| S4 ■ | BASOPHILS | (C2-D3) |
| S5 ■ | MONOCYTES | (C23, D234) |
| S6 ☐ | NEUTROPHILS | (C4-E5) |
| S7 ■ | EOSINOPHILS | (B5-C5) |
| S8 ☐ | T-ALL & B-ALL | (B1-D2) |
| S9 ☐ | AML | (B1-E4) |
| S10 ☐ | AML | (B3-E4) |

AUTOMATIC LINEAGE ASSIGNMENT OF ACUTE LEUKEMIAS BY FLOW CYTOMETRY

This application is a continuation-in-part of application Ser. No. 08/015,709, filed Feb. 9, 1993, now abandoned.

FIELD OF THE INVENTION

The present invention relates to immunophenotyping of normal and abnormal blood cell populations by flow cytometry.

BACKGROUND OF THE INVENTION

Acute leukemias are a heterogeneous group of diseases arising from the clonal expansion of malignant hematopoietic progenitor cells. The heterogeneity of the disease is evidenced by the large diversity of antigenic and light scatter profiles of leukemic cells in patients diagnosed with acute leukemia. This heterogeneity and a poor correlation with normal cell differentiation lead to a lack of consensus in the panel of reagents employed for classification and a lack of uniform criteria for lineage assignment. However, the antigen profiles in acute leukemias are of clinical importance as the various subgroups identified have been associated with different prognoses and serve as a guide for different treatment protocols.

Immunophenotyping by flow cytometry has significantly reduced inter-observer variations in the subclassification of leukemias and has been shown to be particularly powerful in discriminating between myeloid, B-lymphoid and T-lymphoid leukemias. However, traditional flow immunophenotyping may produce biased results due to heterogeneity in leukemias. At the present time there is a lack of consensus in the panel of reagents employed for classification and a lack of uniform criteria for lineage assignment.

Traditional flow immunophenotyping is based on finding an optimal light scatter gate followed by application of marker settings on the immunofluorescence parameters. The distribution of the cells in a display of forward and orthogonal light scatter varies considerably between leukemias, however, and does not fit the normal lymphocyte, blast, monocyte and granulocyte light scatter regions. In addition to difficulties in assessing the appropriate light scatter gate, there are complications arise when attempting to define "negative" versus "positive" immunofluorescence staining in immunophenotyping of leukemias.

In multidimensional flow cytometric analysis the bias which is introduced by employing gates on light scatter parameters is eliminated because all parameters are analyzed simultaneously. Cluster algorithms (Salzman, G. C., et al. 1991. Cytometry Suppl. 5:64), principal components analysis (Leary, J. F., et al. 1988. Cytometry Suppl. 2:99), neural nets (Frankel, D. S., et al. 1989. Cytometry 10:540) and PAINT-A-GATE analysis (U.S. Pat. No. 4,845,653) are among the approaches used for multidimensional analysis. These algorithms permit a more precise identification of cell populations in the multidimensional data space. All require listmode data files in which identical reagents are used. The number of reagents needed for most clinical applications, however, far exceeds the number of available fluorochromes and therefore requires the use of multiple reagent combinations, i.e., running a multi-tube panel with two to three reagents at a time.

The necessity for a large panel of monoclonal antibodies to achieve an optimal lineage assignment of acute leukemias forces the investigator to stain multiple samples using either one, two or three color immunofluorescence. The presence of multiple normal and leukemic cell populations in bone marrow or peripheral blood from patients with leukemia results in a variable number of identifiable cell populations in the samples stained with different antibodies. It is therefore difficult for the investigator to employ objective criteria to assess the antigenic profile of the leukemia. Although the optimal solution to the problem is to determine the antigenic profile in one tube stained with all the required monoclonal antibodies, at the present time not enough different fluorochromes are available.

The present invention employs a novel data analysis method which associates cell populations across tubes and links the positional information of these cell populations to a decision table for classification as normal cells (monocytes, neutrophils, eosinophils, basophils, NK cells, T-lymphocytes and B-lymphocytes) or as leukemic cell populations typical of B-lineage ALL acute lymphoblastic leukemia, T-lineage ALL, AML acute myeloblastic leukemia, AUL acute undifferentiated leukemia, and B-CLL B-lineage chronic lymphocytic leukemia. This approach to data analysis can be generalized to any combination of flow experiments which require data analysis across multiple tubes. The instant use for assigning lineages to acute leukemias is provided by way of example.

SUMMARY OF THE INVENTION

The present invention provides a novel data analysis technique which overcomes the difficulties associated with the analysis and interpretation of data generated by analysis of multiple aliquots of a sample, e.g., the lineage assignment of acute leukemias. The data analysis technique is based on two concepts: 1. Identification of cell clusters, consisting of cells which have similar characteristics within one sample and 2. Identification of cell populations, consisting of cells which exhibit similar characteristics over all samples. In one embodiment, paired combinations of monoclonal antibodies (CD10/CD19, CD20/CD5, CD3/CD22, CD7/CD33, HLA-DR/CD13 and CD34/CD38) conjugated to fluorescent labels are used for immunophenotyping of acute leukemias by fluorescence staining. Eight data files for fluorescence and light scatter are collected on a flow cytometer for each blood or bone marrow sample: an unstained sample, a sample stained with appropriate isotype control antibody-fluorochrome conjugates and samples stained with the six labeled antibody combinations.

The method first clusters the data files utilizing a clustering algorithm. A coordinate system is used to determine the position of each cell cluster in the correlation of forward and orthogonal light scatter. The immunofluorescence intensity of each cell cluster is determined by comparing the background staining of cells with a common parameter in the unstained and isotype control sample. The clusters are then linked across the data files to form cell populations, using the parameter profiles which are common across the data files. The location of each of the cell populations in the now fourteen dimensional feature space is compared with a decision table to make the lineage assignment. Residual erythrocytes, cell debris, normal T lymphocytes, B lymphocytes, NK cells, neutrophils, eosinophils, basophils and monocytes are each expected in a specific region in the fourteen dimensional feature space. By adding boundaries to their frequency, the normal cell populations can be identified in leukemic bone marrow or blood samples. The positions in the fourteen dimensional feature space of the cell populations which do not fulfill the normal criteria are fed to the decision table which outputs their assignment as B-lineage ALL, T-lineage ALL, AML, AUL, B-CLL or as a population of cells of unknown identity.

This data analysis technique employs a new concept for the analysis of flow data in that positional information of cell clusters is matched across multiple aliqouts of a sample. It provides the advantage of more rapid analysis than is possible using conventional immunophenotyping techniques.

DESCRIPTION OF THE DRAWINGS

The file of this patent contains at least one drawing executed in color. Copies of this patent with color drawing(s) will be provided by the Patent and Trademark office upon request and payment of the necessary fee.

FIG. 1A, FIG. 1C and FIG. 1E show the scatter plots for tubes 3, 4 and 5, respectively. FIG. 1B, FIG. 1D and FIG. 1F show the CD19/CD10, CD5/CD20 and CD22/CD3 immunofluoroescent plots for tubes 3, 4 and 5, respectively.

FIG. 4A shows the scatter plot, FIG. 4B shows the plot of CD19/CD10 immunofluorescence, FIG. 4C shows the plot of CD5/CD20 immunofluoresence, FIG. 4D shows the plot of CD22/CD3 immunofluorescence, FIG. 4E shows the plot of CD33/CD7 immunofluorescence, FIG. 4F shows the plot of CD 13/HLA-DR immunofluorescence and FIG. 4G shows the plot of CD38/CD34 immunofluorescence.

FIG. 5A14 FIG. 5G show the cell populations identified by matching clusters identified in FIG. 4A –FIG. 4G. Normal T-lymphocytes are indicated in green and normal monocytes are indicated in blue. The predominant cell population is indicated in red and was identified as a B-lineage acute leukemia. Cells not assigned to the cell populations are depicted in gray. FIG. 5A shows the scatter plot, FIG. 5B, FIG. 5C, FIG. 5D, FIG. 5E, FIG. 5F and FIG. 5G show the plots of CD19/CD10, CD5/CD20, CD22/CD3, CD33/CD7, CD13/HLA-DR and CD38/CD34 immunofluorescence, respectively.

FIG. 6A shows the scatter plot, FIG. 6B shows the plot of CD 19/CD 10 immunofluorescence, FIG. 6C shows the plot of CD5/CD20 immunofluorescence, FIG. 6D shows the plot of CD22/CD3 immunofluorescence, FIG. 6E shows the plot of CD33/CD7 immunofluorescence, FIG. 6F shows the plot of CD13/HLA-DR immunofluorescence and FIG. 6G shows the plot of CD38/CD34 immunofluorescence.

FIG. 7A shows the scatter plot, FIG. 7B, FIG. 7C, FIG. 7D, FIG. 7E, FIG. 7F and FIG. 7G show the plots of CD 19/CD 10, CD5/CD20, CD22/CD3, CD33/CD7, CD 13/HLA-DR and CD38/CD34 immunofluorescence, respectively.

FIG. 8A shows the scatter plot, FIG. 8B shows the plot of CD 19/CD 10 immunofluorescence, FIG. 8C shows the plot of CDS/CD20 immunofluorescence, FIG. 8D shows the plot of CD22/CD3 immunofluorescence, FIG. 8E shows the plot of CD33/CD7 immunofluorescence, FIG. 8F shows the plot of CD13/HLA-DR immunofluorescence and FIG. 8G shows the plot of CD38/CD34 immunofluorescence.

FIG. 9A shows the scatter plot, FIG. 9B, FIG. 9C, FIG. 9D, FIG. 9E, FIG. 9F and FIG. 9G show the plots of CD19/CD10, CD5/CD20, CD22/CD3, CD33/CD7, CD13/HLA-DR and CD38/CD34 immunofluorescence, respectively.

DETAILED DESCRIPTION OF THE INVENTION

Figure 1A:
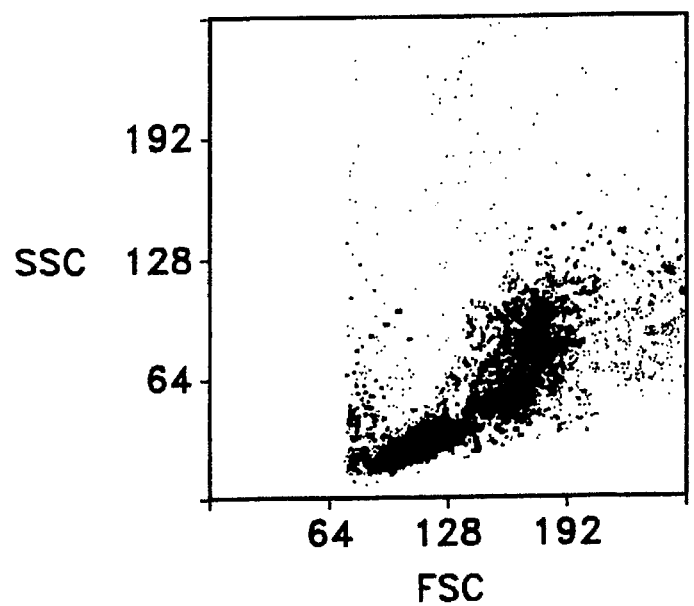
FIG. 1A–FIG. 1F show the clustering results of tubes 3, 4 and 5 of Table 3 in Example 1. Clustering is nonparametric (does not have knowledge of underlying distributions) and does not use a priori information about the cells. At this state the clusters have not yet been identified. Colors are used to indicate cluster membership within a tube but are not relevant across tubes.
Figure 1B:
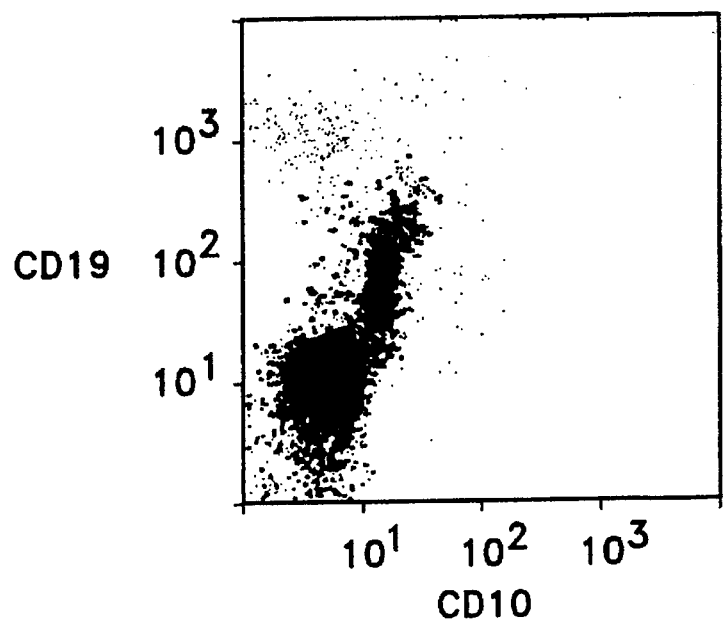
Figure 1C:
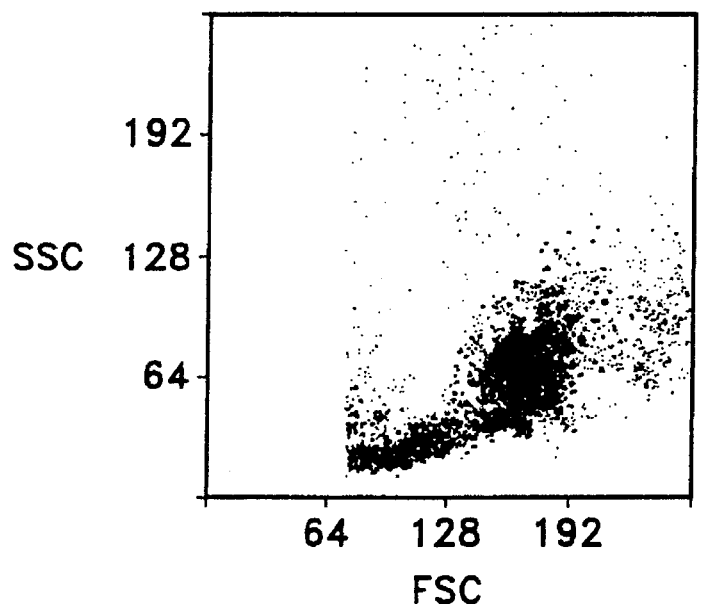
Figure 1D:
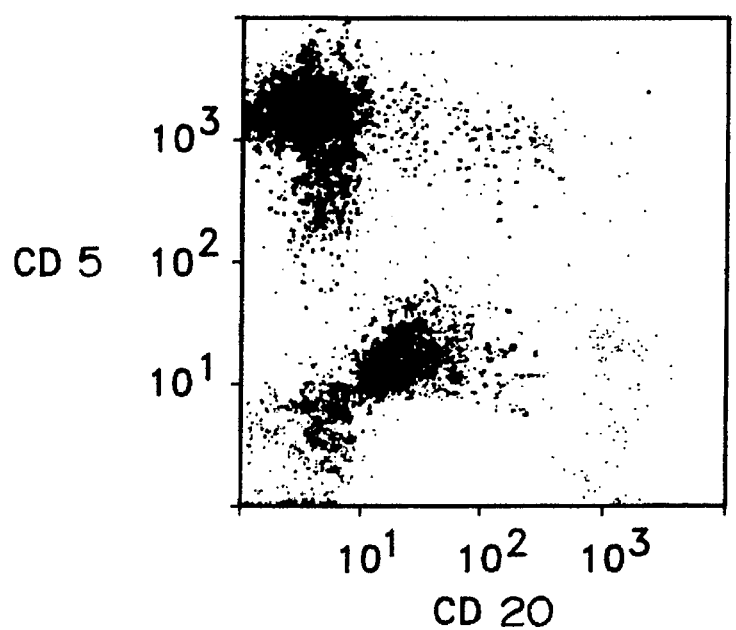
Figure 1E:
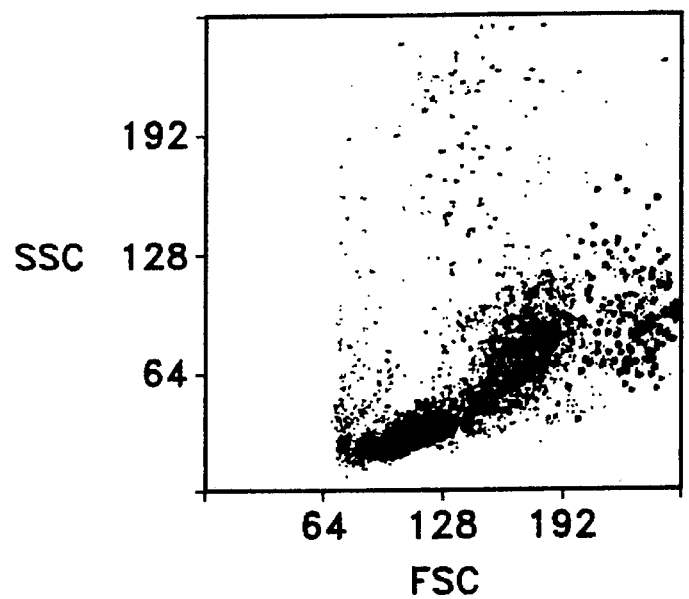
Figure 1F:
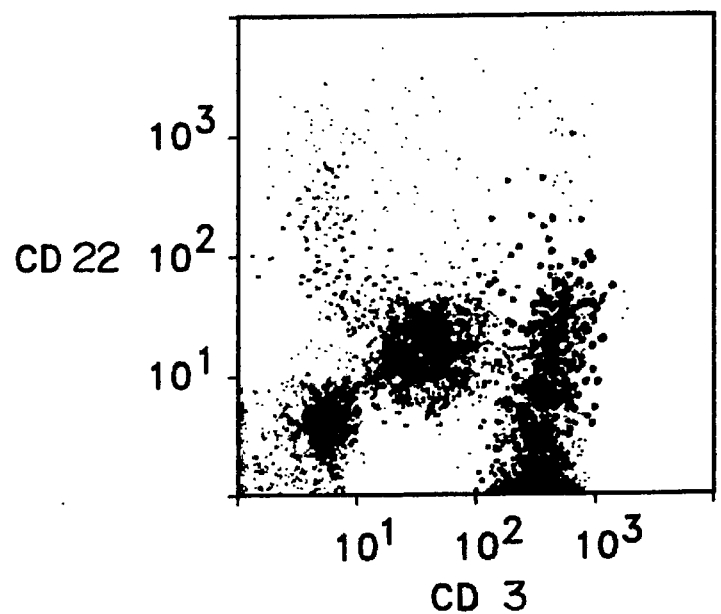

In the inventive data analysis methodology a distinction is made between cell clusters, consisting of cells which have similar characteristics within one tube, and cell populations, consisting of cells which exhibit similar characteristics over all tubes. Cell populations may stain differently in different tubes, but the cells can be associated on the basis of one or more features which remain the same across all tubes, e.g., light scatter properties, the number of cells or a common fluorescence parameter. For example, a possible cell population is identified when the intersection of the scatter profiles of six clusters, one per tube, is not empty. The intersection in this case is calculated on the basis of the light scatter profiles of the cell clusters. Using light scatter as the common parameter across tubes is preferred for its simplicity and because light scatter tends to be less variable than other parameters.

The distinction between cell clusters and cell populations is made to compensate for the lack of a sufficient number of fluorescent colors. For this reason, cell populations must be inferred from multiple data files. For example, if there is a need to measure four colors for a sample with two cell populations and if the flow cytometer only allows simultaneous measurement of two fluorescence parameters, the experiment must be split into two flow cytometer runs. In this case, the cell populations may show different characteristics in one tube (two clusters) but the same characteristics in the other (one cluster). Iin practice, the number of tubes necessary depends on how many fluorescence labels can be measured simultaneously by the instrument. The method of analysis disclosed herein is not limited to two fluorescence colors per tube, and when flow cytometers are used which allow detection of three or more fluorescence parameters additional fluorescence labels may be included in the procedures.

In certain circumstances cell populations may not be deducible from the data. For example, if two clusters are found in a first tube (1a and 1b), two clusters in a second tube (2a and 2b) and the clusters have the same scatter profile, it cannot be deduced whether 1a and 2a or 1a and 2b are from the same cell population. Even clusters of different sizes do not resolve this issue as cells which form a cluster in one tube may not necessarily do so in another tube. For example, if the number of cells in 1a>1b and in 2a>2b, there could be 3 cell populations (X, Y and Z). That is, X and Y may combine in tube 1 to form cluster 1a, with Z forming 1b, and in tube 2 Y and Z combine to form 2a, with X forming 2b.

The solution to this problem is provided by the application domain which assumes that the cells are part of a normal population which exhibits expected normal staining properties. If this hypothesis cannot be falsified, the cells are assumed to be normal and classified as such. Normal cells are then removed from subsequent analysis for identification of abnormal cells. No assumptions can be made about the remaining clusters, and all cell populations are listed. Analysis stops after the possible populations have been identified. In most cases each possible cell population is a real cell population. However, if multiple populations have sufficiently similar light scatter profiles, the inventive algorithm cannot distinguish them.

Identification Of Cell Clusters In a Listmode Data File

Clustering according to the invention may use any of the clustering algorithms known in the art. These include, for example, the isodata (G. H. Ball and D. J. Hall. 1966. Int'l. Nat'l. Commun. Conf., Philadelphia) and K-means algorithms. These and other useful clustering algorithms are described in M. R. Anderberg, *Cluster Analysis for Applications*, Academic Press, New York/London, 1973; P. H. A. Sneath and R. R. Sokal, *Numerical Taxonomy*, Freeman Publishers, San Francisco, 1973; and J. A. Hartigan, *Clustering Algorithms*, John Wiley Publishers, New York, 1975. In a preferred embodiment, the clustering algorithm is a modified algorithm based on the mutual nearest neighbor value (MNN) (Gowda, K. C., et al. 1978. Pattern Recognition 10:405). The MNN of two cells is the sum of the ranks of the cells in their respective nearest neighbor lists (see Gowda et al., reprint page 399, last line to page 400, line 3 and Table 1, page 400, illustrating a typical nearest neighbor list). Two cells are assigned to the same cluster if the MNN is smaller than a preselected threshold T. In the unmodified MNN algorithm the clusters would be determined based on this data alone. However, for flow data it is preferred to use a modified MNN algorithm.

The modification to the MNN algorithm assists in compensating for noise in flow data which can cause errors in clustering. The modified MNN clustering procedure is as follows. After finding a preselected number of nearest neighbors of each cell (k) (Kim, B. S., et al. 1986. IEEE Transactions on Pattern Analysis and Machine Intelligence 8:761), the distance between the cell and each of these neighbors is calculated and added to a global list. The procedure is repeated for all cells in the data file. After sorting the list in order of distance, cells are merged in order of increasing distance to form clusters. Two cells (and the clusters they belong to) are not merged if their clusters exceed a critical size S and the distance between the cells (factor F) is substantially larger than the average distance between cells in each of the clusters. Optionally, a cleanup can be performed after merging in which remaining cells are assigned to clusters close to them. This last step is not usually required for diagnostic applications but is preferred for applications where absolute cell counts are required.

The parameters which can be varied by the user in the modified MNN clustering algorithm to optimize results for a particular application are k=number of neighbors, T=threshold at which two cells are considered neighbors, S=size of the cluster and F=separation factor. The sensitivity of the algorithm to the parameters k and T is low. In general, any value of k between 4 and 6 and T between k and 2*k will give similar results. For analysis of the leukemic data files described herein, K=5, T=7, S=1% and F=1.5–2. These values were obtained by adjustment of the parameters until clusters were found which could be perceived as clusters.

The separation factor F has more weight in the analysis. Different separation factors F may be applied in different sample tubes, depending on the antibody characteristics of the tubes. In the CD7/CD33 and CD34/CD38 tubes of the examples below F was set at 1.5. In the other tubes F was 2.0. This resulted in more clusters identified in the CD7/CD33 and CD34/CD38 tubes and was necessary because of reduced discrimination between cell clusters in those tubes. That is, F is smaller in the tube with CDT-FITC because the separation between T lymphocytes and NK cells expressing CD7 and B lymphocytes with a similar light scatter profile but not expressing CD7 is less than for T lymphocytes identified with CD3.

Coordinate System for Cell Cluster Location

Positional information for the cell clusters is used to established their identity. To optimize the distribution of cell clusters in the light scatter display the orthogonal light scatter parameter is preferably transformed according to the polynomial function $f(x)=14.96+3.09x-0.004x^2+0.0000019x^3$ (in 1,024 resolution) described by L.W.M.M. Terstappen, et al. (1990. Cytometry 11:506–512). The light scatter profile is then defined as a 2-dimensional histogram quantized in 15*15 resolution. To eliminate inter-experiment variability, each experiment is paired with an analysis of normal bone marrow or normal peripheral blood. The mean position of the normal lymphocytes is used to shift the scatter data of the leukemic cells to a position such that the mean of normal T cells falls at absolute channel numbers 110 for FSC and 25 for SSC on a scale of 0–255.

Figure 2:
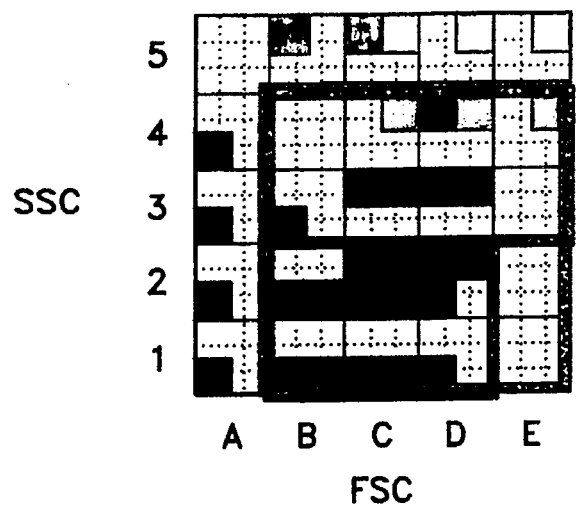
FIG. 2 shows the coordinate system for light scatter profiles, i.e., the bivariate histograms of forward and orthogonal light scatter. The orthogonal light scatter is transformed using a third-order polynomial to increase the separation between the cell clusters. The 15*15 grid represents the internal resolution used by the algorithms.

To specify expected scatter profiles of normal cells, a coarser coordinate system may be established (5*5). FIG. 2 illustrates the regions in which normal erythrocytes, lymphocytes, stem cells, basophils, monocytes, neutrophils and eosinophils are located. A cluster will only be classified as one of these normal cell populations when its mean light scatter value is located within the defined region. The position of the light scatter regions for assignment of leukemia cell clusters is also indicated in FIG. 2.

Figure 3:
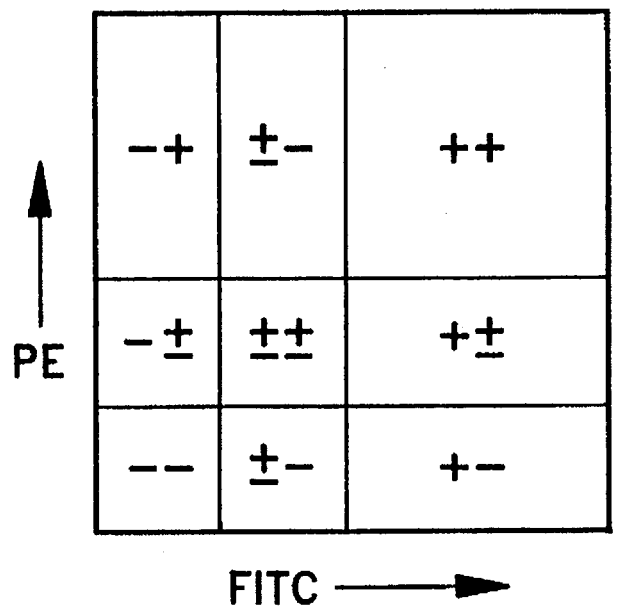
FIG. 3 shows the coordinate system for the immunofluorescence identifiers of the cell clusters. The identifiers are composed of two characters. The first signifies the staining of the cells with the FITC labeled antibody. The second signifies the staining with the PE labeled antibody. A "–" identifier means that the cells did not stain. A "±" identifier means that the cells stained partially. A "+" identifier means that the cells stained fully.

The position of cell clusters in the correlation of two immunofluorescence parameters is assigned one of nine fluorescence identifiers as illustrated in FIG. 3. The assignment is dependent on the position of the cells with the same scatter profile in an isotype control and is based on analyses of the 1-D immunofluorescence histograms of the cells in one cluster. The median of the background staining for both FITC and PE is determined in the isotype control and then compared to the median of the cell cluster in the stained samples. The cluster is considered to express the antigen totally when the ratio between the median of the stained and the isotype sample is larger than two. The cell cluster is considered to express the antigen partially when more than 20% of the cells are positive. A cell is considered positive when its fluorescence intensity exceeds an estimated 0.99 percentile. This 0.99 percentile is defined as the median value plus twice the difference between the 0.87 percentile and the median as it would be for a log normal distribution. This approach to determine whether or not a cell is positive is less sensitive to noise then a direct determination of the 0.99 percentile. When the criteria for positive staining are not fulfilled, the cell cluster did not shift significantly and is considered not to express the antigen defined by the fluorochrome-labeled antibody.

Identification of Normal Cell Populations in Multiple Listmode Data Files

The final assessment for cell populations is based on parts of the cell clusters. Those parts become distinguishable in a combinatorial process in which all clusters are tested gainst each other. In this process all possible combinations of cell clusters (one per tube) are considered, e.g., cluster 1 of tube 3 with cluster 1 of each of tubes 4–8, cluster 2 of tube 3 with cluster 1 of each of tubes 4–8, etc. The combination process sets the minimum value for all bins in the 15*15 scatter profiles of the clusters in the current combination, implemented as a tree structure. That is, bin 1 in the newly constructed 15*15 scatter profiles of the population is the minimum value of bin 1 of the 15*15 scatter profiles of the six cell clusters. The other bins are similarly set. Preferably, the 15*15 scatter profiles of the cell clusters are smoothed with a 3*3 uniform filter to compensate for statistical fluctuations in the scatter data of one cell population over the six tubes. The combination of cell clusters is relevant when the intersection ofo the scatter profiles of the six clusters (1 per tube) is not empty. If the scatter profile resulting from the combinatorial process is not empty (>1% of the cells) a possible cell population is identified.

The properties of the possible cell population are then determined: 1. the number of cells, 2. the area of the scatter profile (the number of bins in the 15*15 histogram which have cells in them), 3. the mean fluorescence values of the unstained and isotype controls, and 4. the immunological profile of the cells. The immunological profile of a cell population is defined by a set of fluorescence identifiers. Each cluster belonging to the population (maximally one per tube) receives a fluorescence identifier. The identifier is based on the fluorescence intensity of those cells of the clusters which fall within the scatter profile of the cell population. In more conventional terminology, the scatter profile of the population defines a gate for the cells of each of the cell clusters.

Table 1 shows the criteria for the properties of normal cell populations, determined using a test set of normal data files. When a normal cell population is identified, the scatter profiles of the clusters contributing to that cell population are updated by subtracting the scatter profile of the normal population from each of the scatter profiles of the six clusters.

Identification of Abnormal Cell Populations in Multiple Listmode Data Files

Once all cells belonging to the normal populations are removed, the characteristics of all possible remaining cell populations are checked in combination against a table of diagnoses (Table 2). In a first stage of analysis, this table preferably takes into account all tubes, although the antibodies in some tubes might not be relevant to the diagnosis. This approach provides more complete information to the user as each population is identified by its clusters in each tube. In a second stage of analysis, only tubes which have an entry on each of the lines in table 3 are checked. This approach maximizes diagnostic effectiveness. This second stage is preferred in cases where a small cluster is obscured by a larger population of normal cells. Matching a small cluster to the appropriate cell population may be impossible because the normal cells, the number of which can differ statistically in the various tubes, are removed. Therefore, when there is evidence for an anomaly, it is preferably reported.

TABLE 1

Criteria for normal cells

| cell type | scat. prof.[1] | auto- fluor.[2] | max % cells | CD10 CD19 | CD20 CD5 | CD3 CD22 | CD7 CD33 | HLADR CD13 | CD34 CD38 |
|---|---|---|---|---|---|---|---|---|---|
| Eryth./debris | S1 | any | 90 | [grid] | [grid] | [grid] | [grid] | [grid] | [grid] |
| T-cells[4] | S2 | low | 80 | [grid] | [grid] | [grid] | [grid] | [grid] | [grid] |
| NK-cells[4] | S2 | low | 20 | [grid] | [grid] | [grid] | [grid] | [grid] | [grid] |
| B-cells[4] | S2 | low | 20 | [grid] | [grid] | [grid] | [grid] | [grid] | [grid] |
| Stemcells | S3 | low | 1 | [grid] | [grid] | [grid] | [grid] | [grid] | [grid] |
| Basophils | S4 | any | 5 | [grid] | [grid] | [grid] | [grid] | [grid] | [grid] |
| Monocytes[4] | S5 | any | 10 | [grid] | [grid] | [grid] | [grid] | [grid] | [grid] |
| Neutrophils | S6 | any | 80 | [grid] | [grid] | [grid] | [grid] | [grid] | [grid] |
| Eosinphils | S7 | high | 10 | [grid] | [grid] | [grid] | [grid] | [grid] | [grid] |

[1]Scatter profile as defined in FIG. 1.
[2]High requires the mean unstained channel number to be larger than 64, low requires a value less than 64
[3]Immunological profile as defined in FIG. 2.
The median of a cluster in a tube has to fall in one of the black colored regions.

 e.g. means that the cluster should be negative for both antibodies.

 e..g means that the cluster should be positive for FL1 and that FL2 is irrelevant

[4]T-Cells, NK-cells, B-cells and Monocytes cannot be scattered over more than 25% of the total dotplot area.

TABLE 2

Criteria for leukemic cells.

| Leukemia lineage | scat. prof. | auto- fluor. | min % cells[1] | CD10 CD19 | CD20 CD5 | CD3 CD22 | CD7 CD33 | HLADR CD13 | CD34 CD38 |
|---|---|---|---|---|---|---|---|---|---|
| B-CLL | S8 | low | 10 | [grid] | [grid] | [grid] | [grid] | [grid] | [grid] |
| B-ALL | S8 | low | 5 | [grid] | 2 | | | | 3 |
|  | S8 | low | 10 | [grid] | [grid] | | | | 3 |
|  | S8 | low | 5 | [grid] | [grid] | | | | 3 |
|  | S8 | low | 10 | [grid] | | [grid] | | | 3 |

TABLE 2-continued

Criteria for leukemic cells.

| Leukemia lineage | scat. prof. | auto-fluor. | min % cells[1] | immunological profile | | | | | |
|---|---|---|---|---|---|---|---|---|---|
| | | | | CD10 CD19 | CD20 CD5 | CD3 CD22 | CD7 CD33 | HLADR CD13 | CD34 CD38 |
| | S8 | low | 5 | ▦ | | ▦ | | | 3 |
| | S8 | low | 10 | ▦ | ▦ | ▦ | | | 3 |
| | S8 | low | 5 | ▦ | ▦ | ▦ | | | 3 |
| | S8 | low | 10 | ▦ | ▦ | ▦ | | | 3 |
| | S8 | low | 1 | ▦ | ▦ | ▦ | | | ▦ |
| | S8 | low | 1 | ▦ | ▦ | | | ▦ | ▦ |
| | S8 | low | 1 | ▦ | | ▦ | | ▦ | ▦ |
| | S8 | low | 1 | ▦ | | | ▦ | ▦ | ▦ |
| | S8 | low | 1 | ▦ | ▦ | | ▦ | ▦ | ▦ |
| | S8 | low | 1 | ▦ | ▦ | | ▦ | ▦ | ▦ |
| | S8 | low | 1 | ▦ | | ▦ | ▦ | ▦ | ▦ |
| | S8 | low | 1 | | | ▦ | ▦ | ▦ | ▦ |
| | S8 | low | 1 | ▦ | ▦ | ▦ | ▦ | ▦ | ▦ |
| T-All | S8 | low | 5 | ▦ | ▦ | ▦ | | | ▦ |
| | S8 | low | 5 | ▦ | ▦ | ▦ | ▦ | | |
| | S8 | low | 5 | ▦ | ▦ | ▦ | ▦ | ▦ | |
| | S8 | low | 5 | ▦ | ▦ | ▦ | ▦ | | |
| | S8 | low | 5 | | ▦ | | | ▦ | |
| | S8 | low | 5 | ▦ | ▦ | ▦ | ▦ | ▦ | ▦ |
| AML | S9 | — | 5 | ▦ | ▦ | ▦ | ▦ | ▦ | ▦ |

TABLE 2-continued

Criteria for leukemic cells.

| Leukemia lineage | scat. prof. | auto-fluor. | min % cells[1] | CD10 CD19 | CD20 CD5 | CD3 CD22 | CD7 CD33 | HLADR CD13 | CD34 CD38 |
|---|---|---|---|---|---|---|---|---|---|
| | S9 | — | 5 | ▨ | ▨ | ▨ | ▨ | ▨ | ▨ |
| | S9 | — | 5 | ▨ | ▨ | ▨ | ▨ | ▨ | ▨ |
| | S9 | — | 5 | | ▨ | | ▨ | ▨ | ▨ |
| | S10 | — | 5 | ▨ | ▨ | | | ▨ | |
| | S10 | — | 5 | ▨ | ▨ | | ▨ | | |
| AUL | S2 | low | 5 | ▨ | ▨ | ▨ | ▨ | ▨ | ▨ |

[1]The percentages are low if the requirements of the immulogical profile are strict.
[2]If no region for the cluster is specified the position of the cluster in that tube is not tested.
[3]If CD34 positive, minimum % of leukemic cells goes down to 1%.

EXAMPLE 1

AUTOMATED LINEAGE ASSIGNMENT OF ACUTE LEUKEMIAS

Mononuclear cells from bone marrow aspirates of B-lineage ALL, T-lineage ALL and AML patients were separated on FICOLL-HYPAQUE (Sigma Chemical Co., St. Louis, Mo.) and immunofluorescently labeled following the protocol of the Acute Leukemia Phenotyping Kit (Becton Dickinson Immunocytometry Systems (BDIS), San Jose, Calif.). The antibody combinations used were as shown in Table 3:

TABLE 3

Antibody Combinations

| | FITC Labeled | PE Labeled |
|---|---|---|
| Tube 1 | Unstained | Unstained |
| Tube 2 | Isotype (IgG2a) | Isotype (IgG1) |
| Tube 3 | CD10 (CALLA) | CD19 (Leu12) |
| Tube 4 | CD20 (Leu6) | CD5 (Leu1) |
| Tube 5 | CD3 (Leu4) | CD22 (Leu14) |
| Tube 6 | CD7 (Leu9) | CD33 (LeuM9) |
| Tube 7 | HLADR | CD13 (LeuM7) |
| Tube 8 | CD34 (HPCA-2) | CD38 (Leu17) |

Flow cytometric analysis was performed on a FACSCAN (BDIS). The instrument was prepared for sample analysis using CALIBRITE Beads and AUTOCOMP software (BDIS). Data acquisition was performed using LYSYS 2.0 Software (BDIS). Forward light scatter, orthogonal light scatter and the two log (4 decade) amplified fluorescence signals were measured for 10000 cells and the data stored in listmode data files. Data from 5000 cells were used for analysis to reduce processing time. Forward and orthogonal light scatter detectors were adjusted using normal blood as a control during instrument setup. Lymphocytes were found between channels 50 and 150 for FSC and just above channel 0 for SSC. Normal sample data was saved for later calibration of sample scatter data. The data analysis algorithms were developed using C++ on SUN Sparcstations and Macintosh PC's.

FIG. 4A–FIG. 4G shows the clustering result of 5000 cells of a patient with an acute B-lymphoid leukemia. In each of the fluorescence displays the cell clusters found were assigned a color in order of decreasing percentage per tube (plotting colors in one tube have no relationship to plotting colors in other tubes). Scatter positions and immunofluorescence identifiers for the clusters are shown in the following table:

| | MONOCYTES 3.1% | | | | MONOCYTES 2.9% | | | | T-CELLS 4.3% | | | | B-ALL 59.0% | | | |
|---|---|---|---|---|---|---|---|---|---|---|---|---|---|---|---|---|
| | % | SC | FL1 | FL2 | % | SC | FL1 | FL2 | % | SC | FL1 | FL2 | % | SC | FL1 | FL2 |
| 3 | 11.1 | E3 | CD10– | CD19– | 8.5 | C2 | CD10– | CD19– | 8.5 | C2 | CD10– | CD19– | 70.6 | C2 | CD10– | CD19+ |
| 4 | 81.0 | C2 | CD20– | CD5– | 81.0 | C2 | CD20– | CD5– | 7.7 | C2 | CD20– | CD5+ | 81.0 | C2 | CD20– | CD5– |
| 5 | 11.7 | D3 | CD3– | CD22– | 11.7 | D3 | CD3– | CD22– | 6.8 | C2 | CD3+ | CD22– | 66.2 | C2 | CD3– | CD22+ |
| 6 | 3.4 | E3 | CD7– | CD33± | 3.3 | E5 | CD7± | CD33– | 7.0 | C2 | CD7+ | CD33– | 84.1 | C2 | CD7– | CD33± |
| 7 | 73.2 | C2 | DR+ | CD13– | 73.2 | C2 | DR+ | CD13– | 73.2 | C2 | DR+ | CD13– | 73.2 | C2 | DR+ | CD13– |
| 8 | 6.4 | D3 | CD34– | CD38+ | 8.1 | C2 | CD34– | CD38± | 8.1 | C2 | CD34– | CD38± | 72.6 | C2 | CD34+ | CD38+ |

The clusters are shown in immunofluorescence dotplots but were identified in four-dimensional space.

Figure 4A:
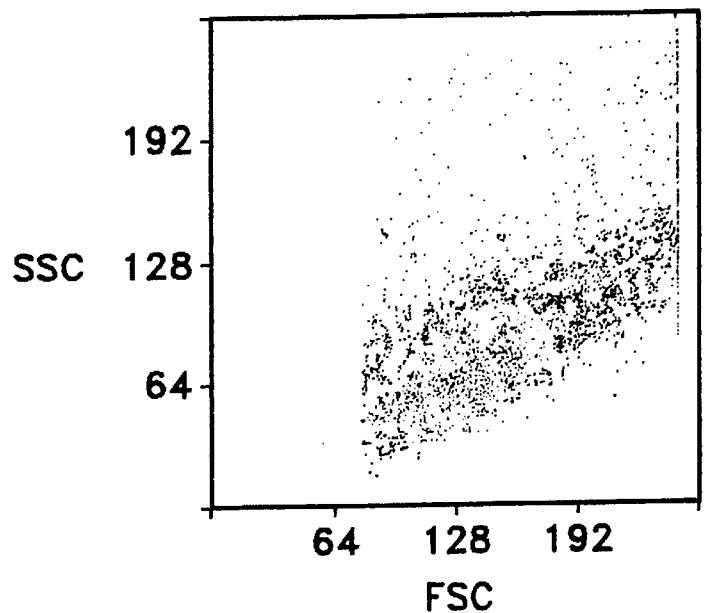
FIG. 4A–FIG. 4G show clustering of listmode data files using data from a patient with acute B-lymphoid leukemia. Colors are assigned in order of cluster size and cannot be used to link clusters from one panel to another at this stage.
Figure 4B:
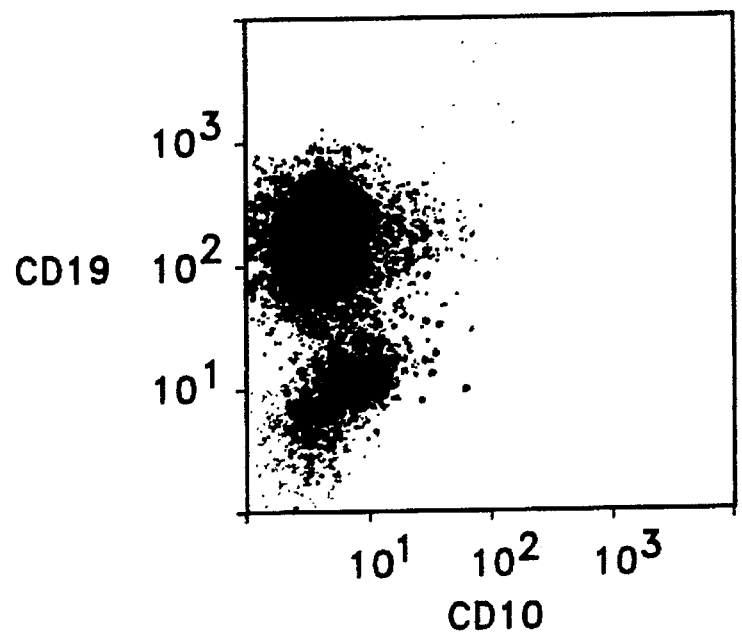
Figure 4C:
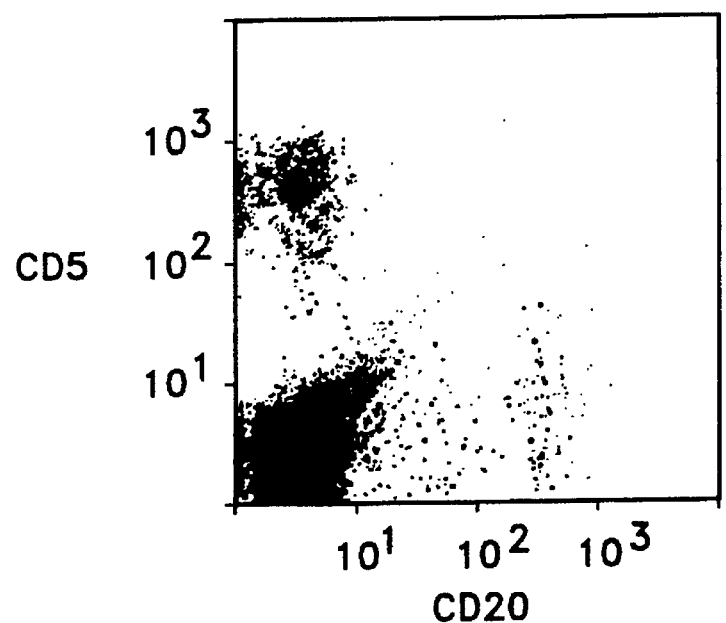
Figure 4D:
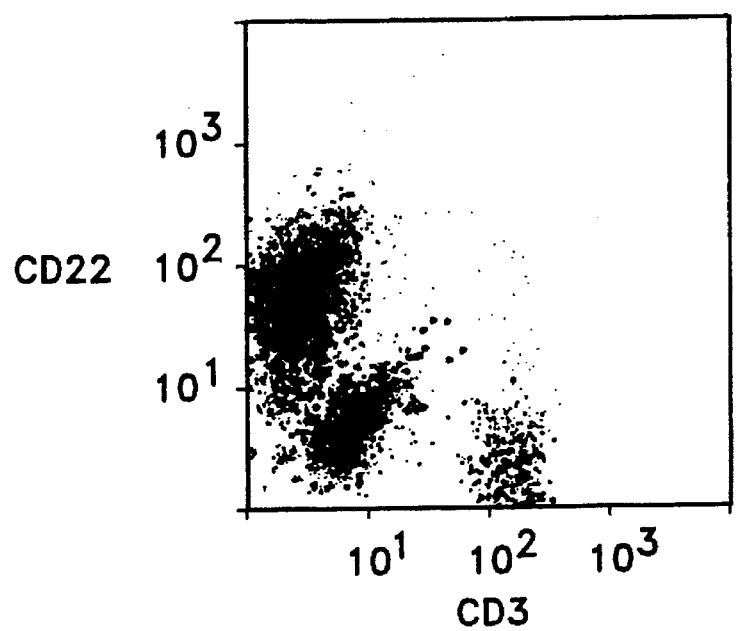
Figure 4E:
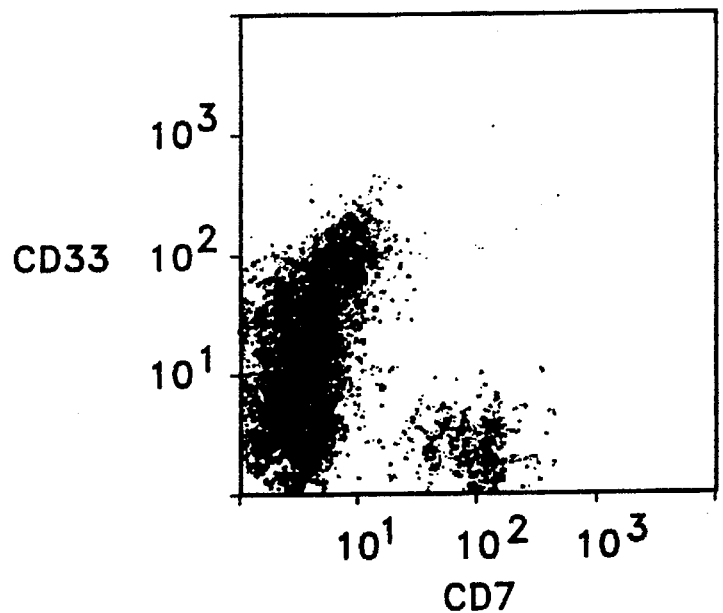
Figure 4F:
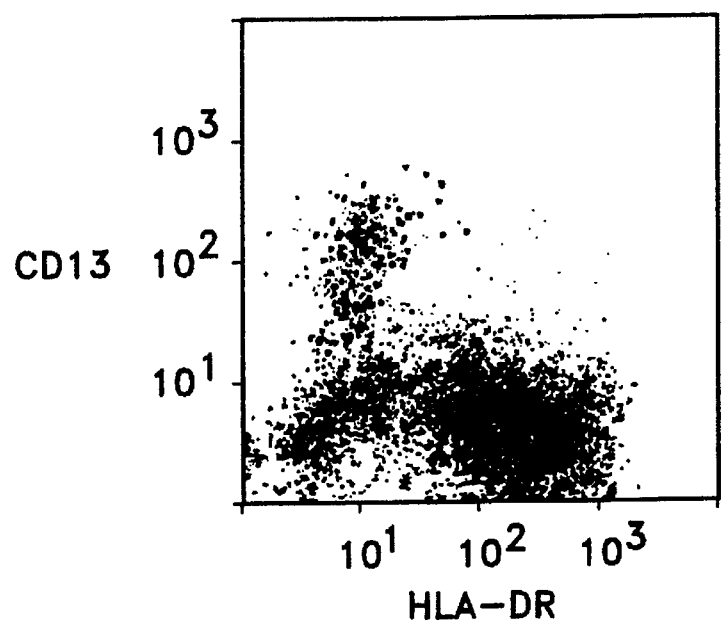
Figure 4G:
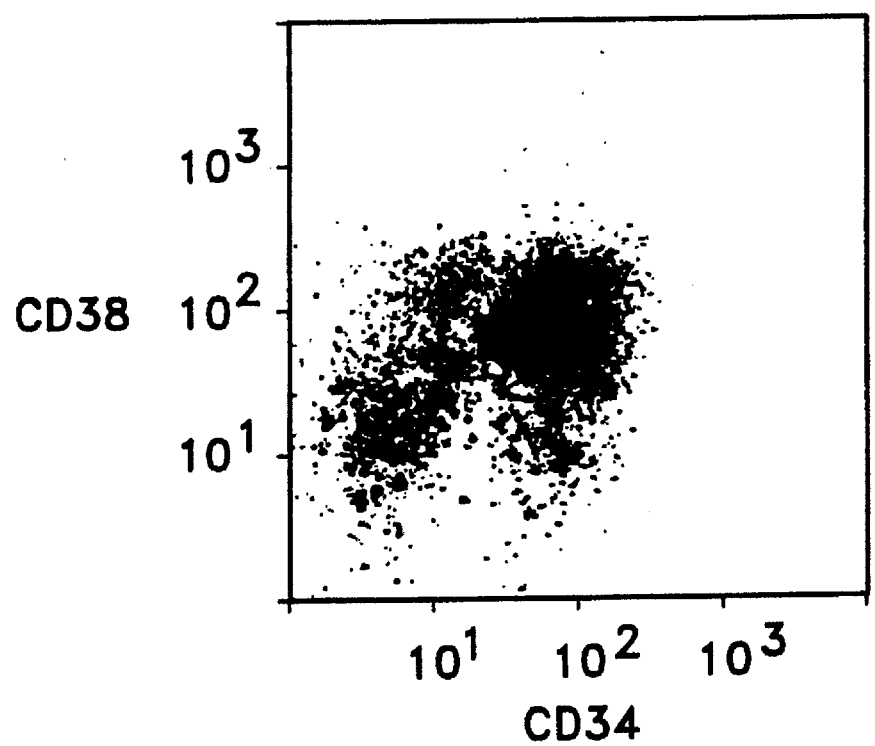
Figure 5A:
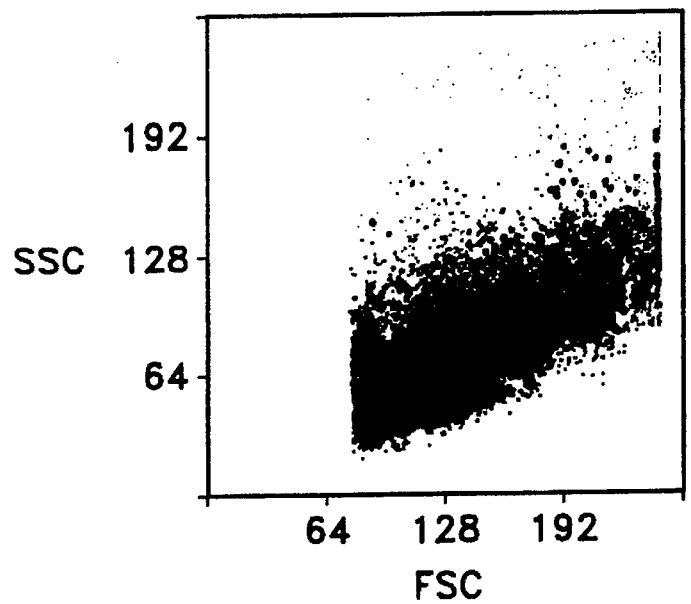
Figure 5B:
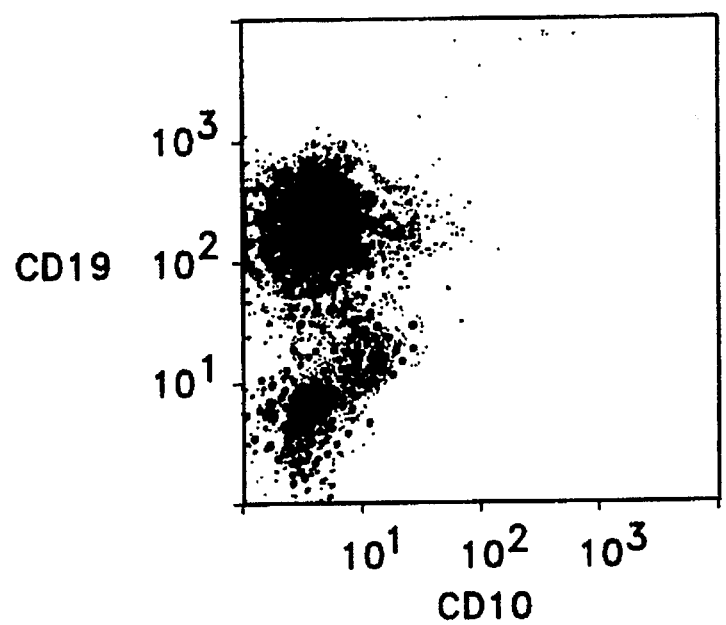
Figure 5C:
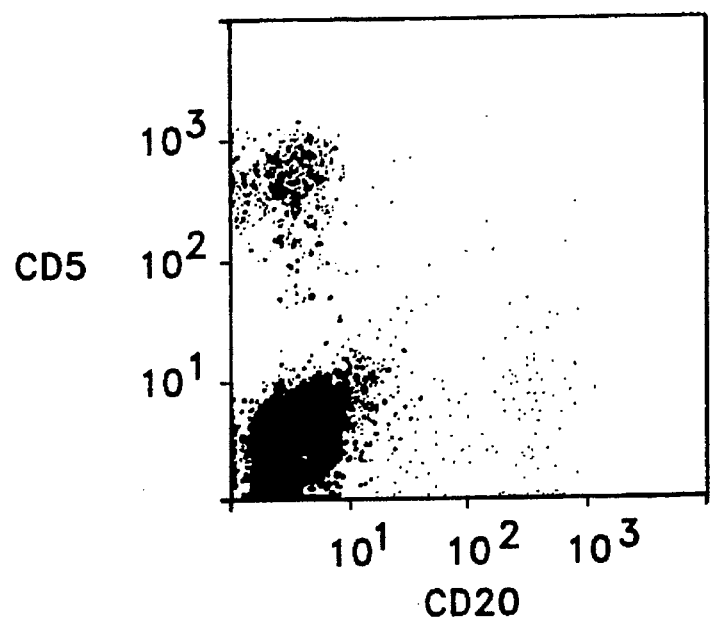
Figure 5D:
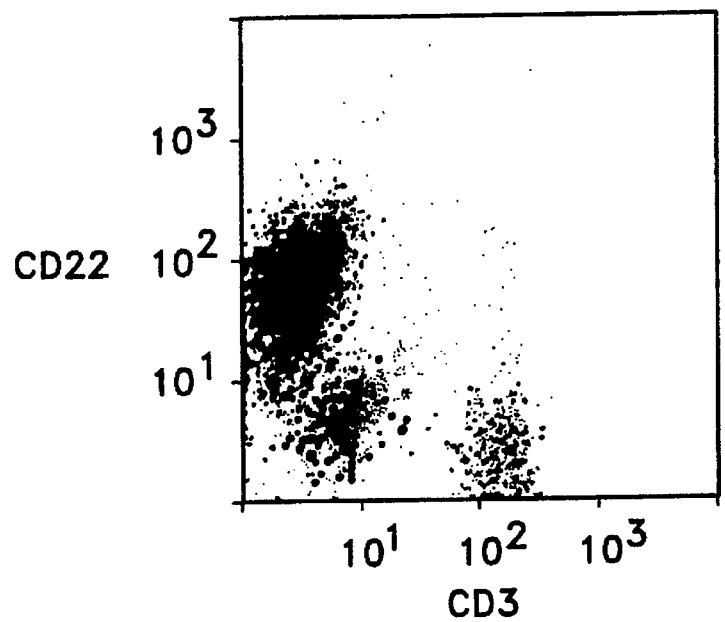
Figure 5E:
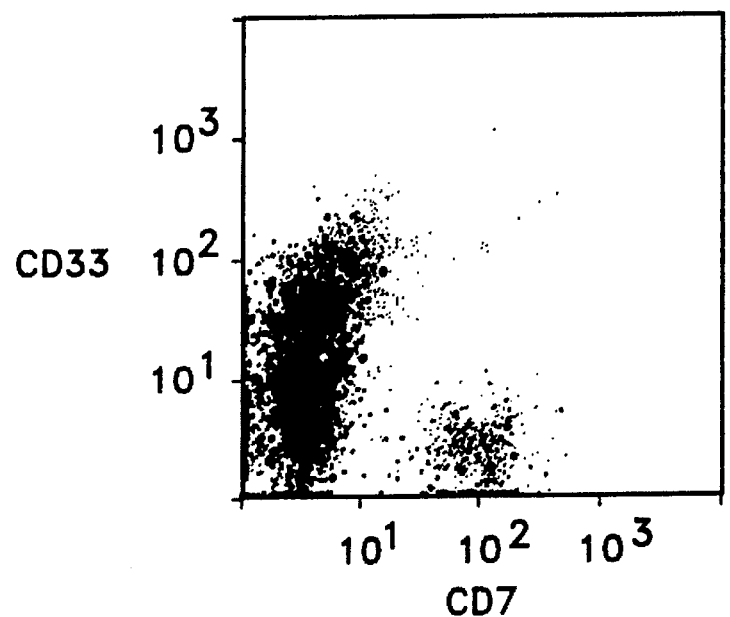
Figure 5F:
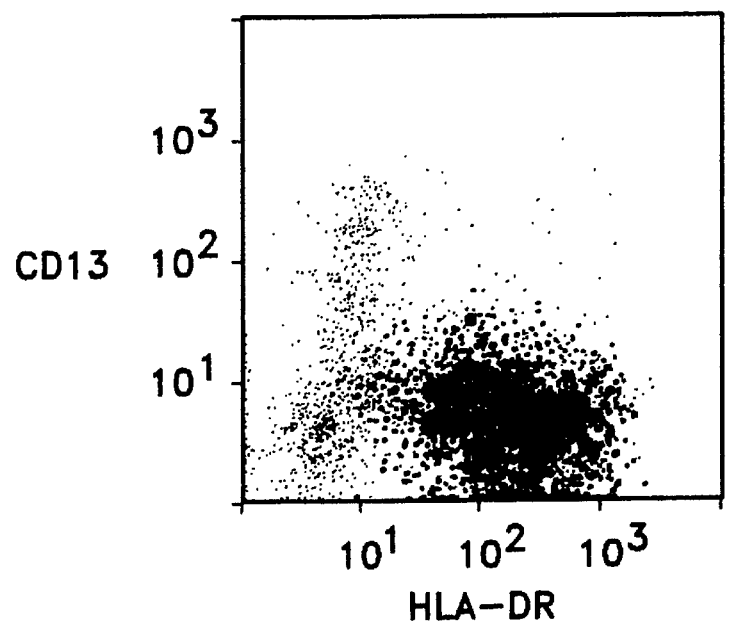
Figure 5G:
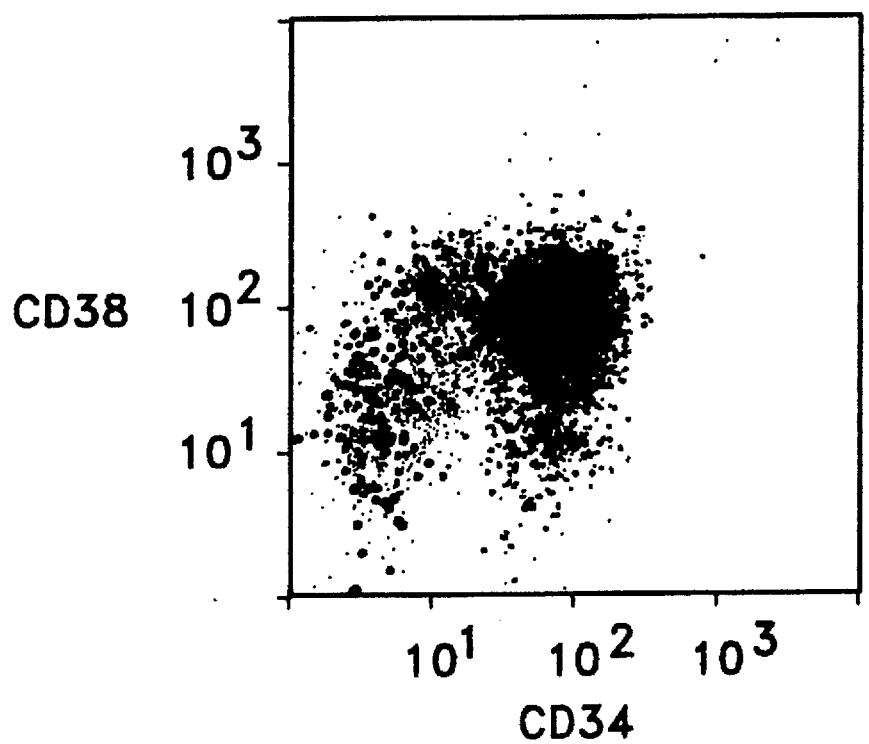
Figure 6A:
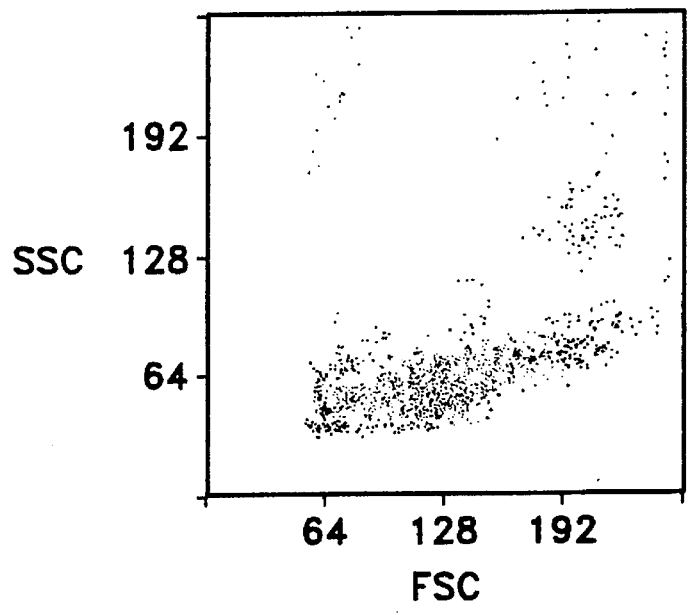
FIG. 6A–FIG. 6G show clustering of listmode data files using data from a patient with acute T-lymphoid leukemia. Colors are assigned in order of cluster size and cannot be used to link clusters from one panel to another at this stage.
Figure 6B:
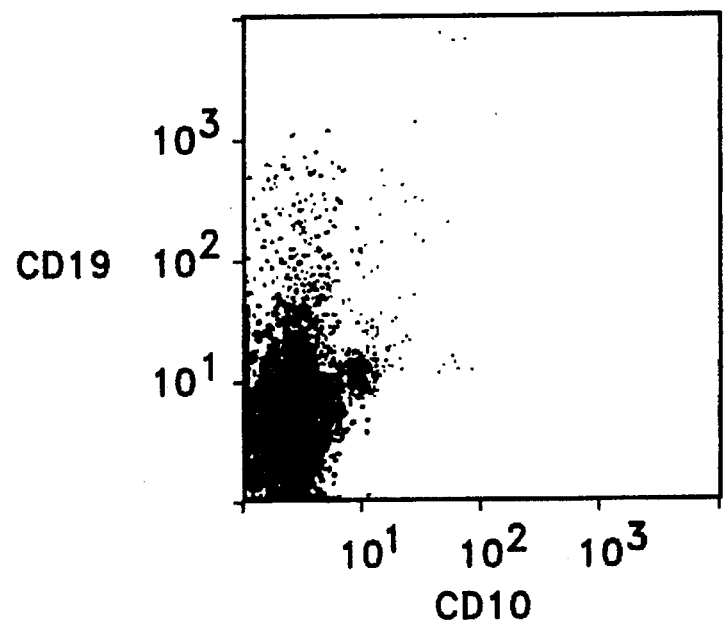
Figure 6C:
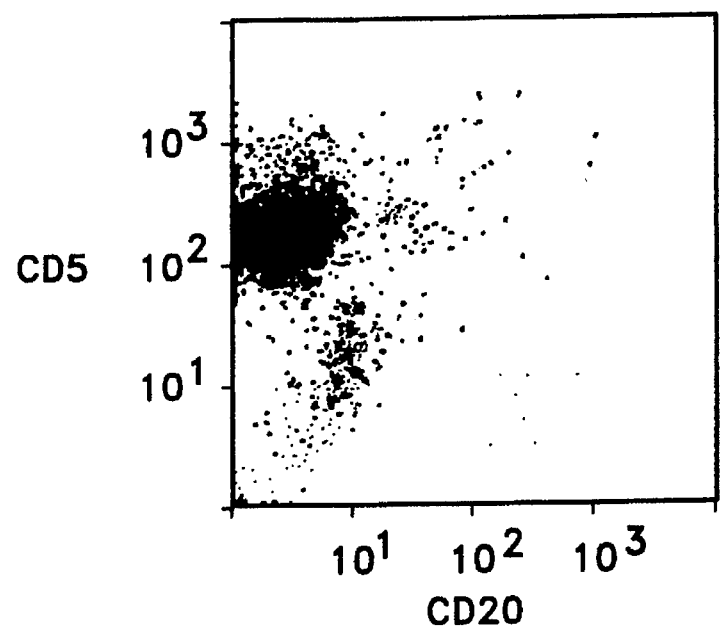
Figure 6D:
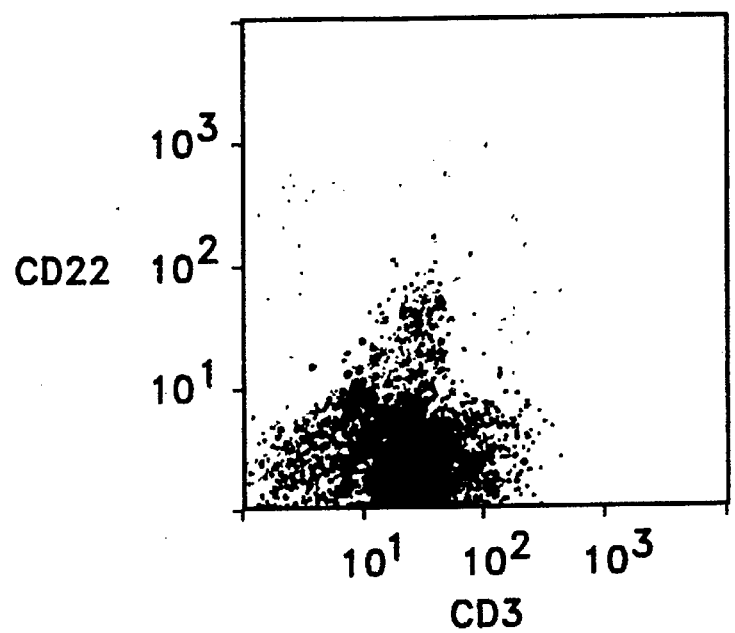
Figure 6E:
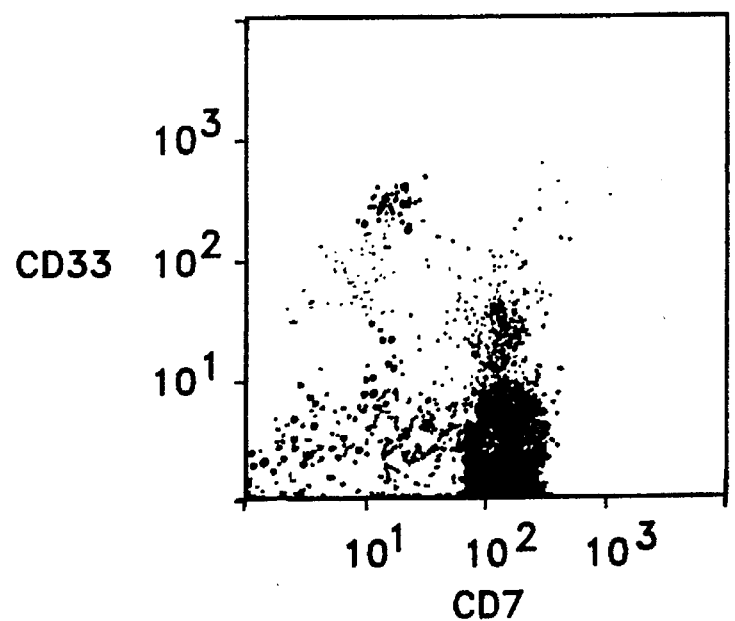
Figure 6F:
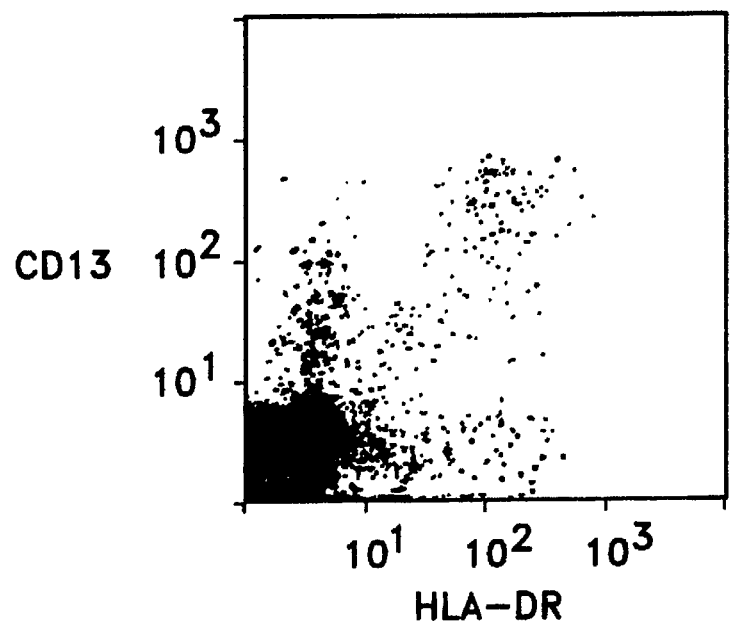
Figure 6G:
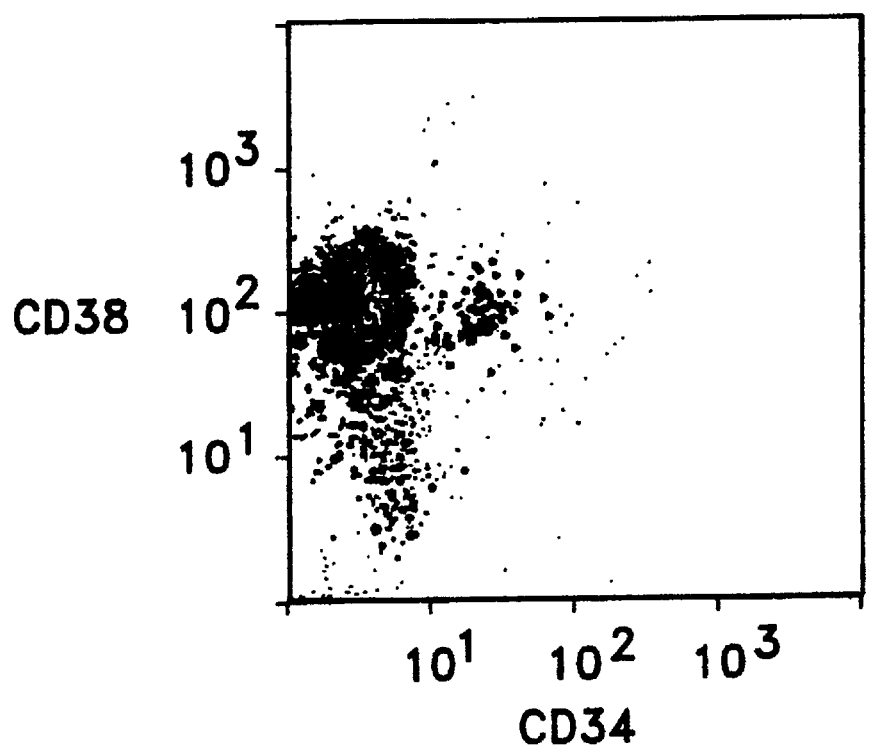
Figure 7A:
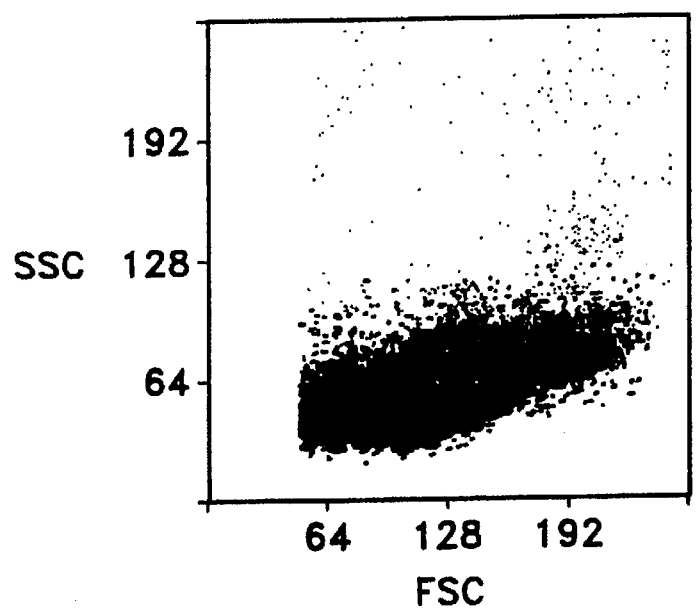
FIG. 7A–FIG. 7G show the cell populations identified by matching clusters identified in FIG. 6A–FIG. 6G. Normal T-lymphocytes are indicated in green. The predominant cell population is indicated in red and was identified as a T-lineage acute leukemia. Cells not assigned to the cell populations are depicted in gray.
Figure 7B:
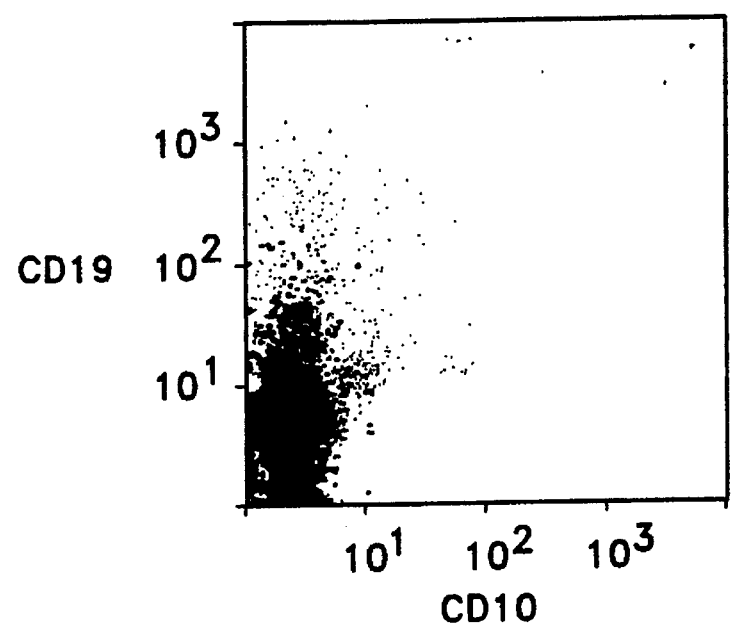
Figure 7C:
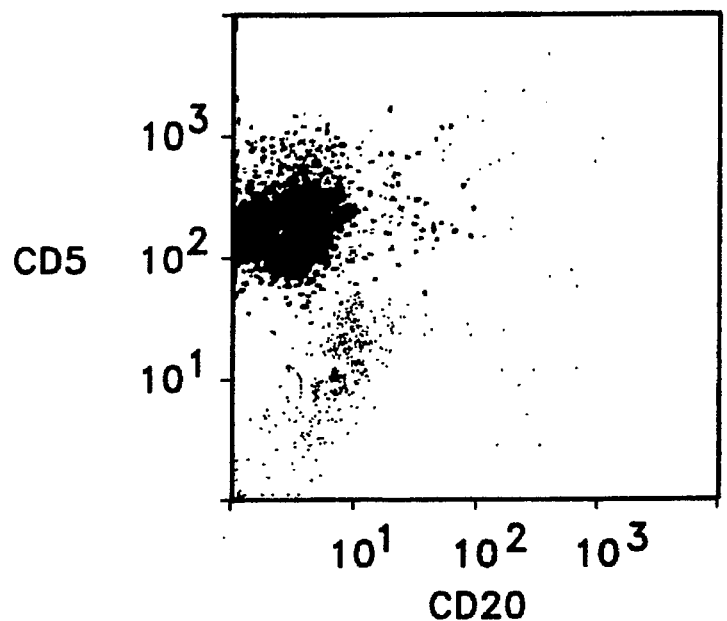
Figure 7D:
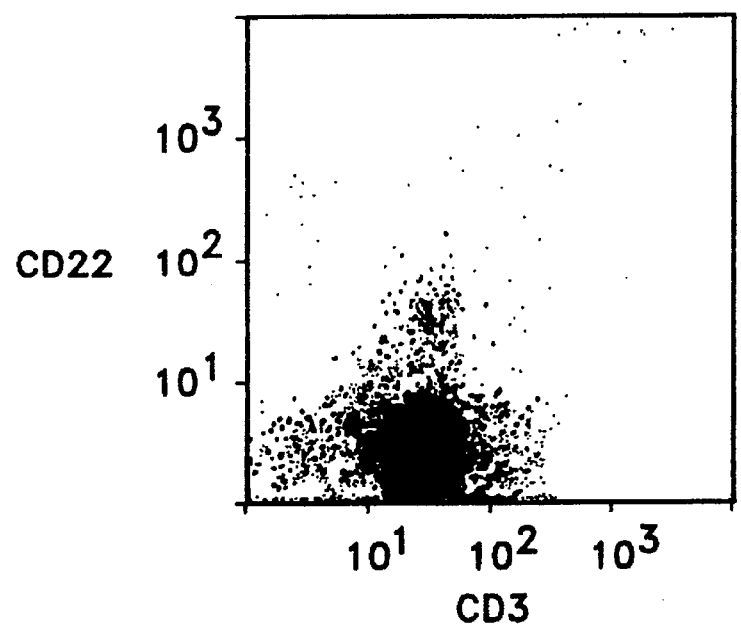
Figure 7E:
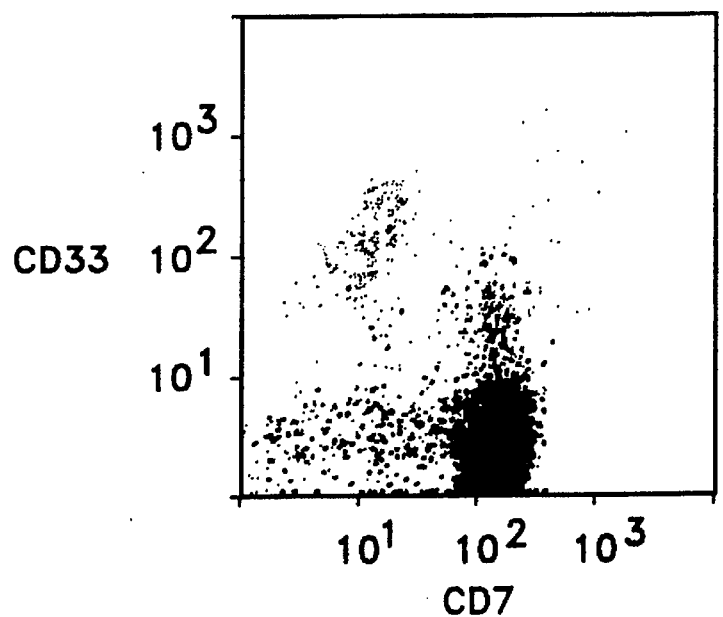
Figure 7F:
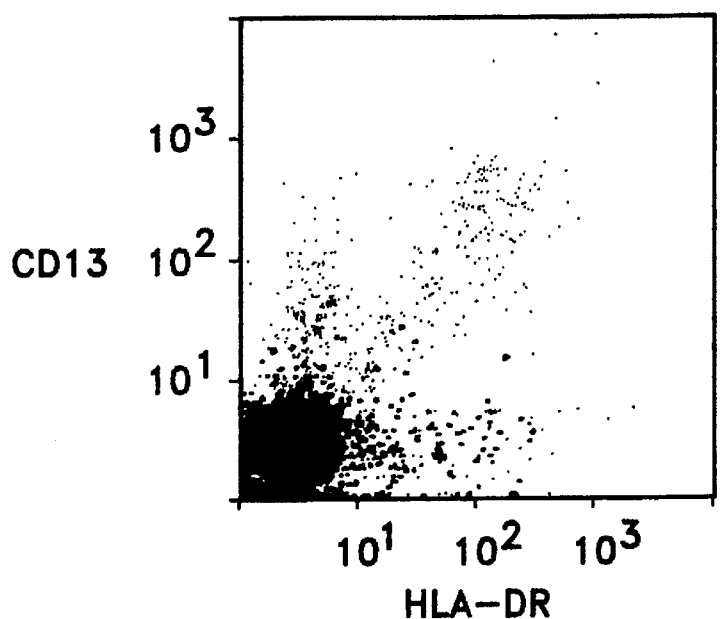
Figure 7G:
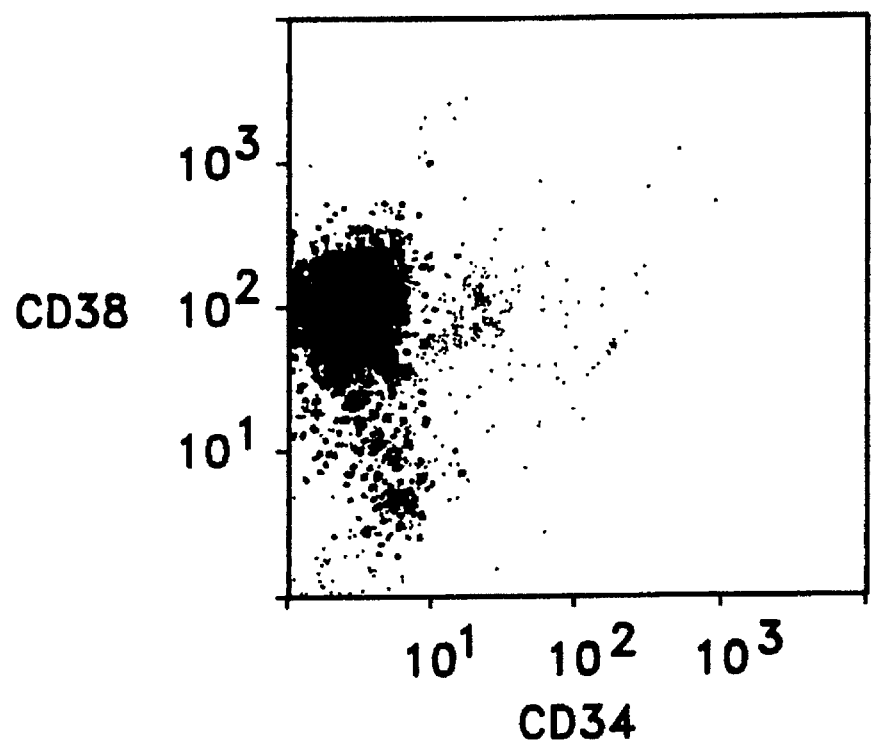

For example, in FIG. 4B (tube 3) five clusters were found: 1. a cluster plotted in red with a frequency of 70.6%, located in a light scatter region C2, staining with CD19 but not with CD10; 2. a cluster plotted in green with a frequency of 11.1%, located in a light scatter region E3, not staining with CD10 and CD19; 3. a cluster plotted in blue present in a frequency of 8.5%, located in a light scatter region C2, not staining with CD10 and CD19; 4. a cluster plotted in purple present in a frequency of 5.1%, located in a light scatter region E3, staining with CD19 but not with CD10 and 5. a cluster plotted in dark blue with a frequency of 2.2% and located in a light scatter region E5 and not staining with CD10 and CD19. Immunofluorescence identifiers are preliminary and were not used to identify cell populations.

After the data files were clustered, the algorithm was used to search for normal cell populations and eliminate them from the analysis by subtracting the population scatter histogram from the cluster scatter histogram. The algorithm then searched for the presence of abnormal cell populations.

In FIG. 5A–FIG. 5G, the result of the population search is illustrated with the colors now matched across tubes. The population statistics (% of cells belonging to each population) are given in the above table showing the scatter positions and immunofluorescence identifiers for the clusters in FIG. 4A–FIG. 4G. The cell populations found were normal T cells (4.3%) plotted in green, normal monocytes plotted in blue (6.0%) and a cell population identified as B-lineage ALL plotted in red (59.0%). The percentages quoted for the populations are based on the overlap of the clusters in the scatter space and therefore represent a lower boundary. For example, although the frequency of the predominant cell cluster was greater than 66.2% in all of the samples, the frequency of the leukemic cell population which is composed of portions of the various cell clusters is only 59.0%. The initial identifiers assigned to the clusters may differ from the identifiers assigned to the clusters of the cell populations because the cells of each cluster are gated with the scatter histogram of the population.

The data files of a patient with acute T-lymphoid leukemia were similarly clustered (FIG. 6). In FIG. 6B (tube 3) three clusters were found, in FIG. 6C (tube 4) three, FIG. 6D (tube 5) six, FIG. 6E (tube 6) five, FIG. 6F (tube 7) four and in FIG. 6G (tube 8) five. The scatter positions and immunofluorescence identifiers for these clusters are given in the following table:

Correlating the light scatter positional information across tubes indicated the presence of a population of cells which fulfilled the criteria of normal T lymphocytes, plotted in green in FIG. 7A–FIG. 7G. A second population of cells was found and classified as T-lineage ALL, plotted in red in FIG. 7A–7G. The population statistics (% of cells belonging to each population) are given in the above table showing the scatter positions and immunofluorescence identifiers for the clusters in FIG. 6A–FIG. 6G. In this case, the frequency and position of the cluster in the sixth tube (CD34/CD38) discriminated between normal T-cells and malignant T-cells.

Figure 8A:
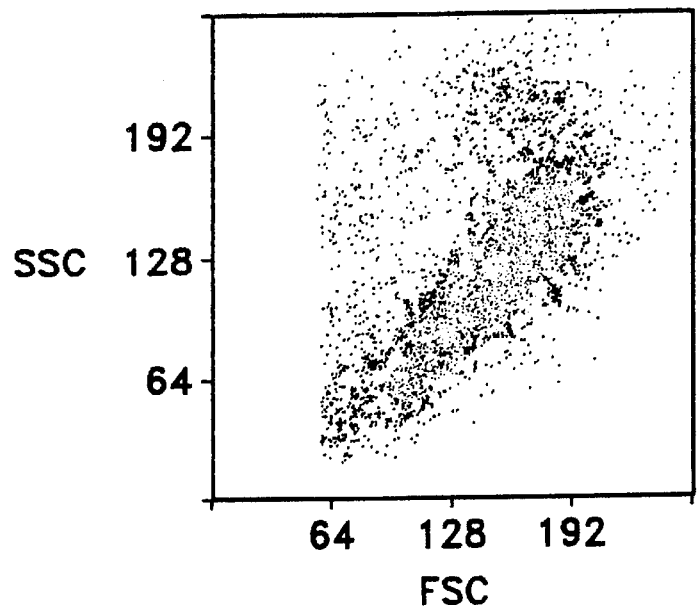
FIG. 8A–FIG. 8G show clustering of listmode data files using data from a patient with acute myeloid leukemia. Colors are assigned in order of cluster size and cannot be used to link clusters from one panel to another at this stage.
Figure 8B:
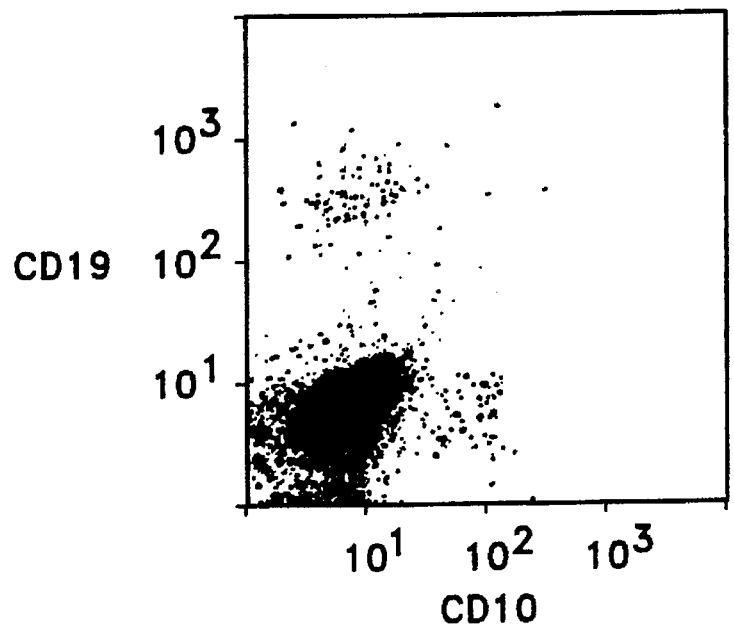
Figure 8C:
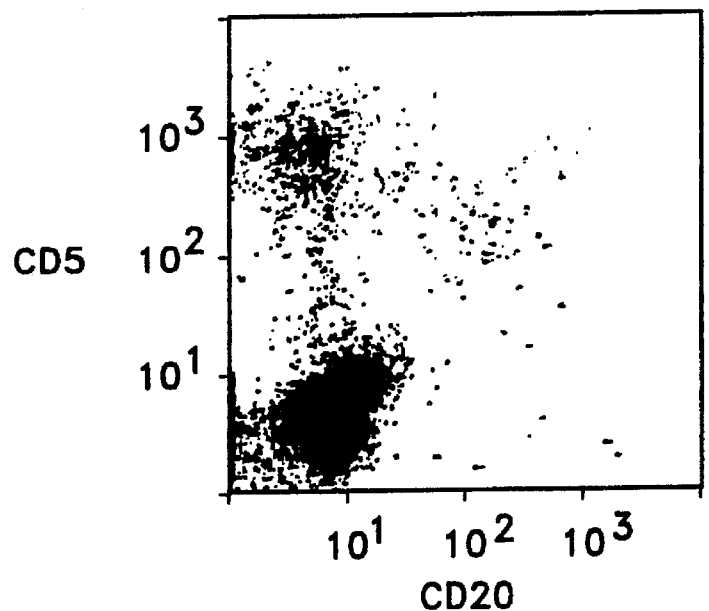
Figure 8D:
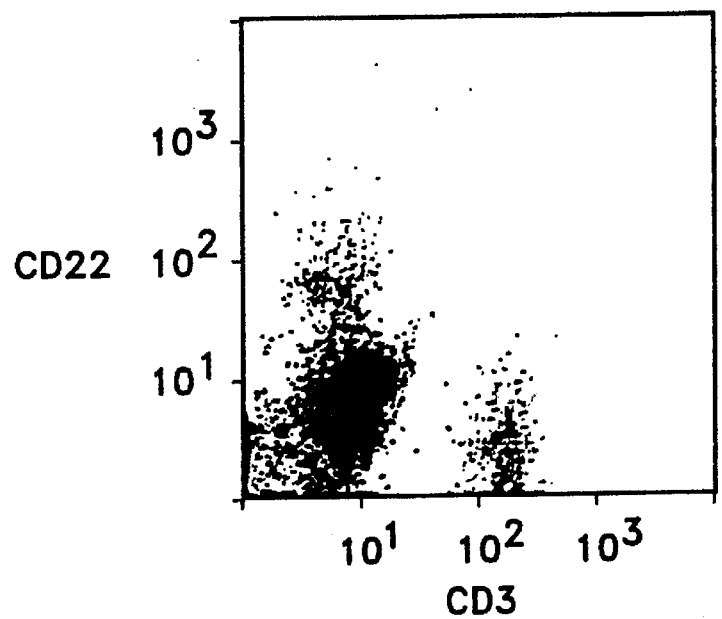
Figure 8E:
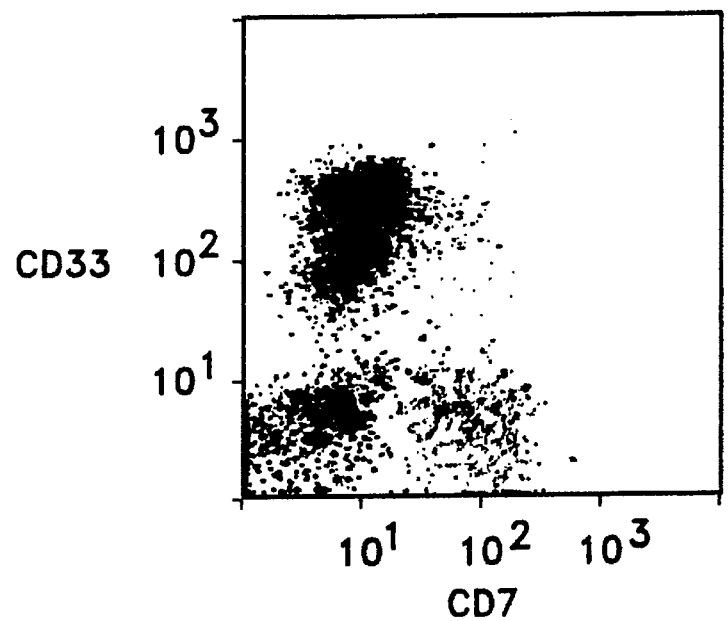
Figure 8F:
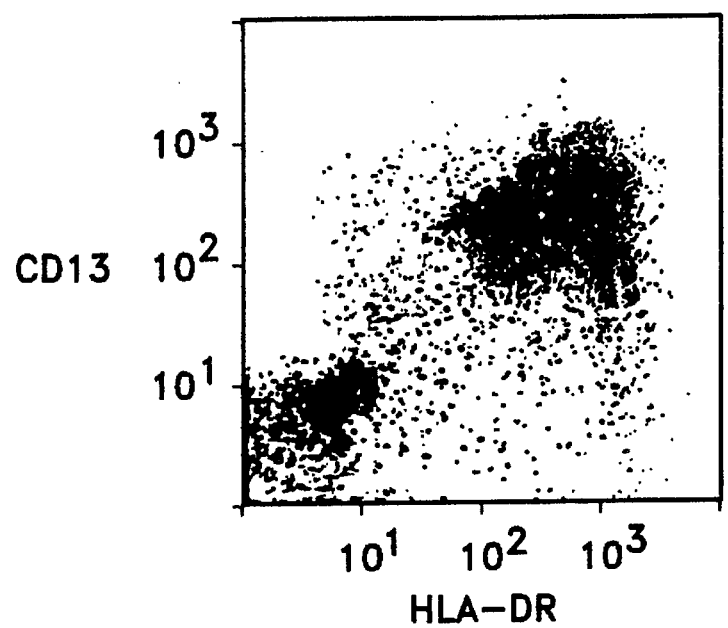
Figure 8G:
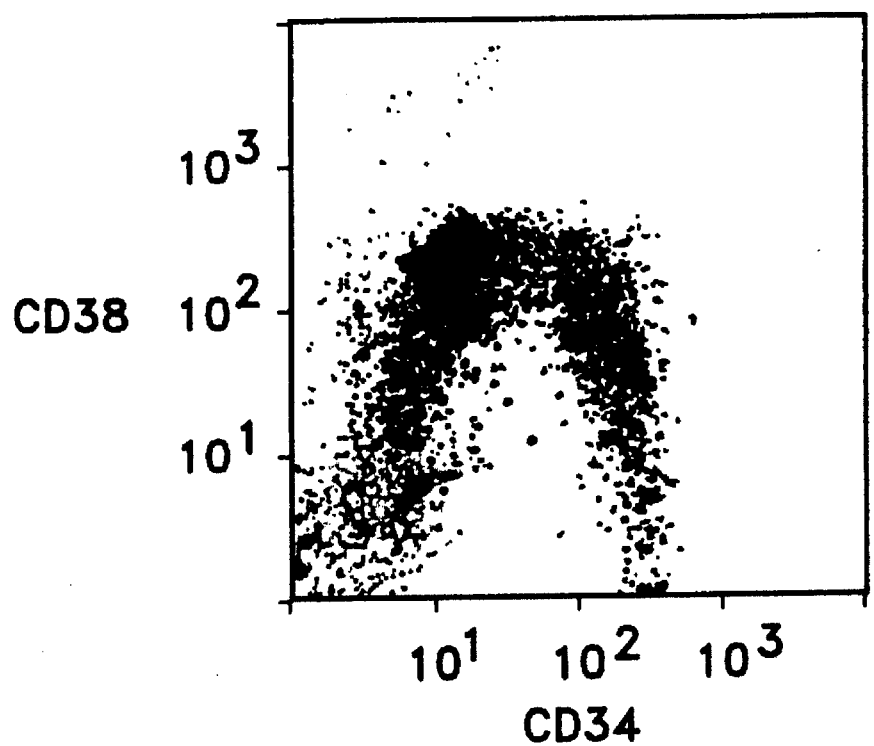
Figure 9A:
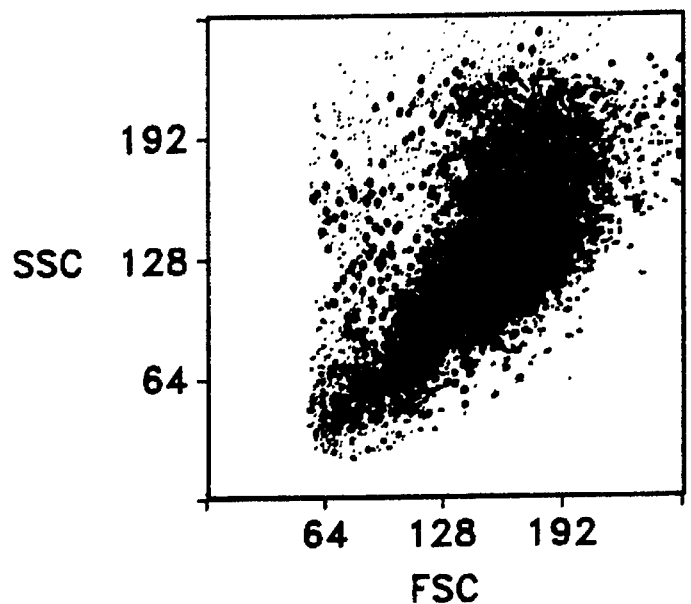
FIG. 9A–FIG. 9G show the cell populations identified by matching clusters identified in FIG. 8A–FIG. 8G. Normal T-lymphocytes are indicated in green and normal monocytes in blue. The predominant cell population is indicated in red and was identified as an acute myeloid leukemia. Cells not assigned to the cell populations are depicted in gray.
Figure 9B:
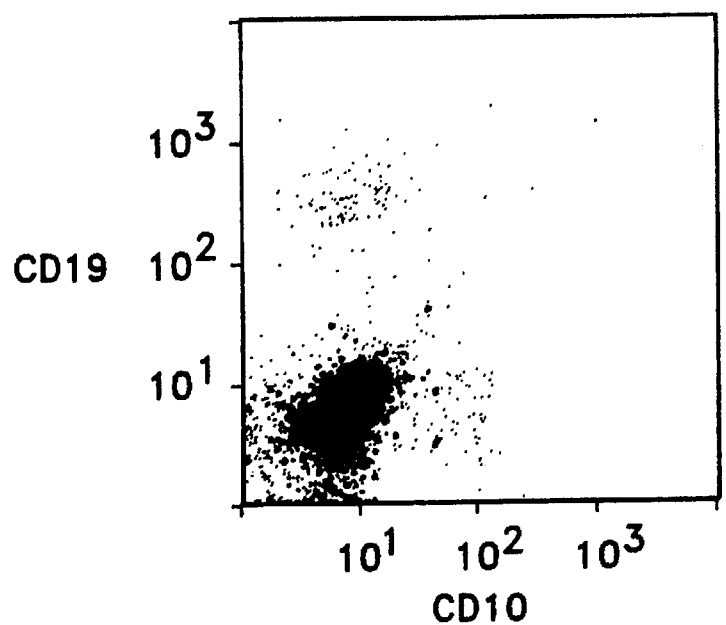
Figure 9C:
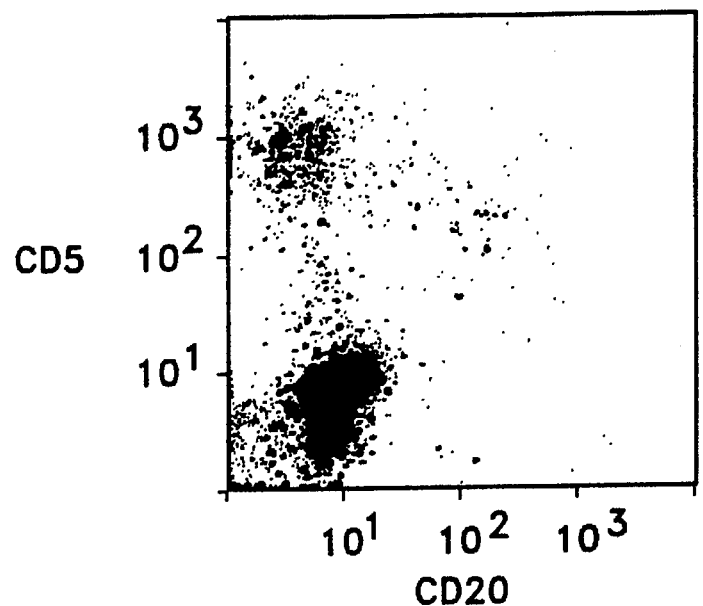
Figure 9D:
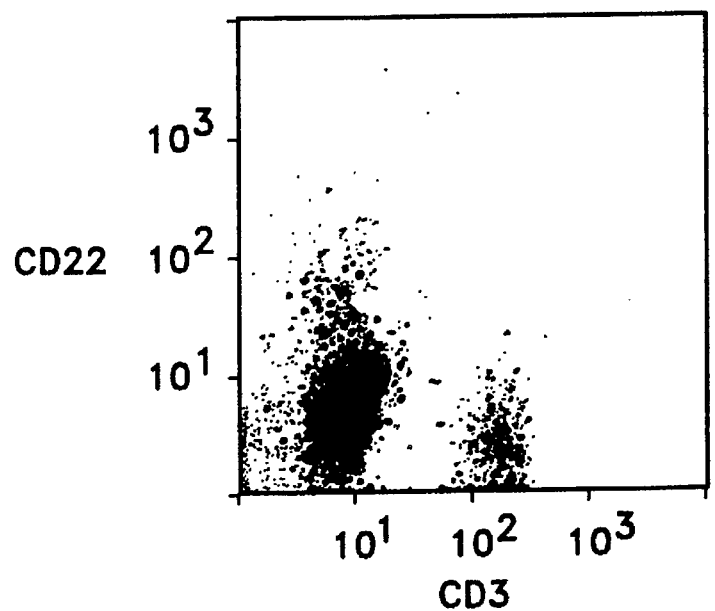
Figure 9E:
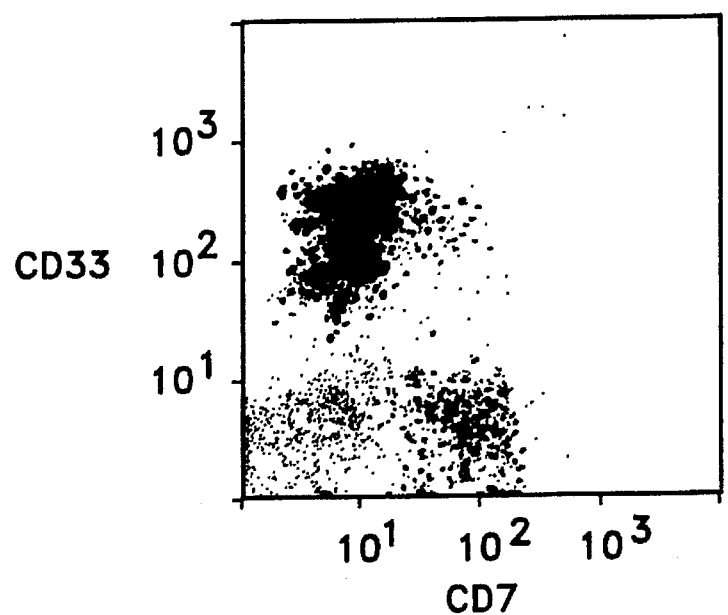
Figure 9F:
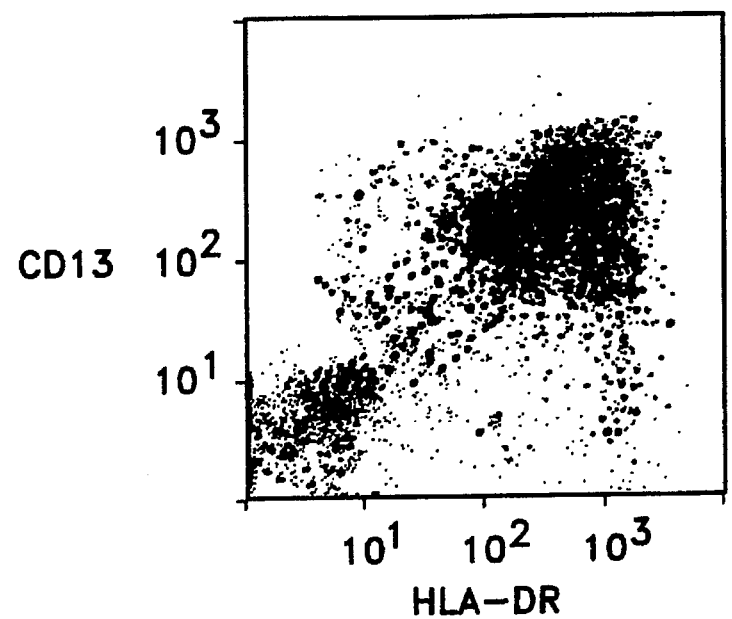
Figure 9G:
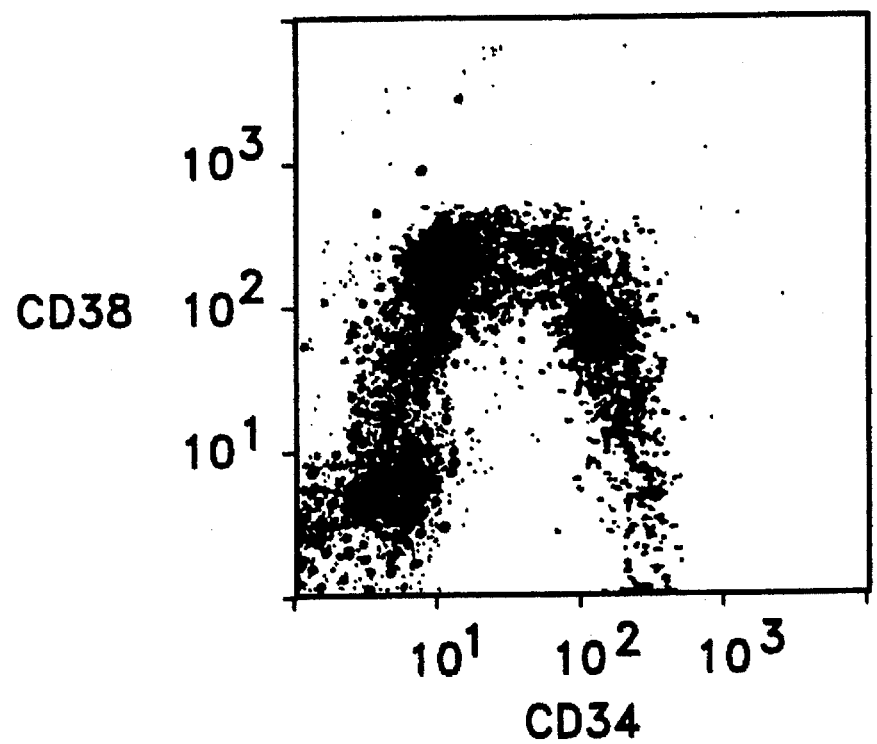

The clustering of the data files of a patient with acute myeloid leukemia is shown in FIG. 8A–FIG. 8G. In FIG. 8B (tube 3) four clusters were found, in FIG. 8C (tube 4) two, FIG. 8D (tube 5) four, FIG. 8E (tube 6) four, FIG. 8F (tube 7) four and in FIG. 8G (tube 8) five. The scatter positions and immunofluorescence identifiers for these clusters are shown in the following table:

| | T-CELLS 3.0% | | | | T-ALL 68.5% | | | | T-ALL 7.0% | | |
|---|---|---|---|---|---|---|---|---|---|---|---|
| | % | SC | FL1 | FL2 | % | SC | FL1 | FL2 | % | SC | FL1 | FL2 |
| 3 | 92.7 | C2 | CD10– | CD19– | 92.7 | C2 | CD10– | CD19– | 92.7 | C2 | CD10– | CD19– |
| 4 | 92.8 | C2 | CD20– | CD5+ | 92.8 | C2 | CD20– | CD5+ | 92.8 | C2 | CD20– | CD5+ |
| 5 | 79.6 | C2 | CD3+ | CD22– | 79.6 | C2 | CD3+ | CD22– | 79.6 | C2 | CD3+ | CD22– |
| 6 | 84.2 | C2 | CD7+ | CD33– | 84.2 | C2 | CD7+ | CD33– | 84.2 | C2 | CD7+ | CD33– |
| 7 | 89.5 | C2 | DR– | CD13– | 89.5 | C2 | DR– | CD13– | 89.5 | C2 | DR– | CD13– |
| 8 | 3.0 | C2 | CD34– | CD38– | 74.0 | C2 | CD34– | CD38+ | 11.4 | C2 | CD34– | CD38+ |

| T-CELLS 6.6% | | | | MONOCYTES 2.6% | | | | MONOCYTES 7.4% | | | |
|---|---|---|---|---|---|---|---|---|---|---|---|
| % | SC | FL1 | FL2 | % | SC | FL1 | FL2 | % | SC | FL1 | FL2 |
| 3 | 88.0 | D3 | CD10– | CD19– | 88.0 | D3 | CD10– | CD19– | 88.0 | D3 | CD10– | CD19– |
| 4 | 12.0 | C2 | CD20– | CD5+ | 85.2 | D3 | CD20– | CD5– | 85.2 | D3 | CD20– | CD5– |
| 5 | 9.2 | C2 | CD3+ | CD22– | 72.9 | D3 | CD3– | CD22– | 72.9 | D3 | CD3– | CD22– |
| 6 | 11.1 | C2 | CD7+ | CD33– | 68.1 | D3 | CD7– | CD33+ | 68.1 | D3 | CD7– | CD33+ |
| 7 | 25.5 | B2 | DR– | CD13± | 7.2 | C5 | DR± | CD13± | 61.9 | D3 | DR+ | CD13+ |
| 8 | 27.4 | C2 | CD34– | CD38± | 33.1 | D3 | CD34– | CD38+ | 27.4 | C2 | CD34– | CD38± |

| | AML 29.0% | | | | AML 23.6% | | | |
|---|---|---|---|---|---|---|---|---|
| | % | SC | FL1 | FL2 | % | SC | FL1 | FL2 |
| 3 | 88.0 | D3 | CD10– | CD19– | 88.0 | D3 | CD10– | CD19– |
| 4 | 85.2 | D3 | CD20– | CD5– | 85.2 | D3 | CD20– | CD5– |
| 5 | 72.9 | D3 | CD3– | CD22– | 72.9 | D3 | CD3– | CD22– |
| 6 | 68.1 | D3 | CD7– | CD33– | 68.1 | D3 | CD7– | CD33– |
| 7 | 61.9 | D3 | DR+ | CD13+ | 61.9 | D3 | DR+ | CD13+ |
| 8 | 33.1 | D3 | CD34– | CD38+ | 27.5 | D3 | CD34+ | CD38+ |

By correlating the light scatter positional information across tubes three cell populations were found, as shown in FIG. 9A–FIG. 9G. The population statistics (% of cells belonging to each population) are given in the above table showing the scatter positions and immunofluorescence identifiers for the clusters in FIG. 8A–FIG. 8G. The cell population plotted in green was classified as a normal T-cell population, the population plotted in dark blue contained monocytes and the cell population plotted in red was classified as AML. In this experiment, cell population classified as monocytes consisted of two populations which differed slightly in their locations. Additionally, two cell populations identified as AML were identified which only differed in the sixth tube. For a clinical report, these populations could be added together. Reporting all populations found, however, more clearly illustrates the algorithm used to find the cell populations. In this case, the cells classified as monocytes most likely belong to the leukemia. However, the criteria to classify these cell populations as leukemic were not met.

What is claimed is:

1. A method for determining the lineage of acute leukemia cells in a sample by flow cytometry comprising:

a) staining a first aliquot of the sample with CD10 conjugated to the first fluorochrome and CD 19 conjugated to the second fluorochrome, staining a second aliquot of the sample with CD20 conjugated to the first fluorochrome and CD5 conjugated to the second fluorochrome, staining a third aliquot of the sample with CD3 conjugated to the first fluorochrome and CD22 conjugated to the second fluorochrome, staining a fourth aliquot of the sample with CD7 conjugated to the first fluorochrome and CD33 conjugated to the second fluorochrome, staining a fifth aliquot of the sample with HLA-DR conjugated to the first fluorochrome and CD 13 conjugated to the second fluorochrome, and staining a sixth aliquot of the sample with CD34 conjugated to the first fluorochrome and CD38 conjugated to the second fluorochrome, the first and second fluorochromes being distinguishable by flow cytometry;

b) analyzing the stained first, second, third, fourth, fifth and sixth aliquots by flow cytometry, acquiring list-mode data files for forward light scatter, orthogonal light scatter, first fluorochrome fluorescence and second fluorochrome fluorescence for each aliquot;

c) identifying cell clusters in each of the first, second, third, fourth, filth and sixth aliquots using the acquired forward light scatter, orthogonal light scatter, first fluorochrome fluorescence and second fluorochrome fluorescence data;

d) establishing a scatter profile for each cluster identified in step (c);

e) identifying cell populations by correlating the scatter profiles of the clusters in each aliquot in a combinatorial process and identifying clusters which have common scatter profiles, thereby establishing a scatter profile for each cell population;

f) determining an immunological profile for each cell population identified using the fluorescence data of those cells of each cluster which fall within the scatter profile of cell population;

g) identifying normal cell populations by comparing the immunological profile and scatter profile of each cell population to a scatter profile and immunological profile expected for normal cells;

h) subtracting the scatter profile of the normal cell population from the scatter profile of each cluster containing cells belonging to the normal cell population, and;

i) determining the lineage of remaining abnormal cell populations by comparing the scatter profiles and immunological profiles of the abnormal cell populations to scatter profiles and immunological profiles expected for known leukemic cell populations.

2. The method of claim 1 wherein
   the immunological profiles and scatter profiles of the abnormal cell populations are compared to the immunological profiles and scatter profiles of leukemic cell populations selected from the group consisting of B-lineage ALL, T-lineage ALL, AML, AUL and B-CLL.

3. The method according to claim 2 wherein the first fluorochrome is FITC and the second fluorochrome is PE.

* * * * *